(12) United States Patent
Mitas et al.

(10) Patent No.: US 7,981,616 B2
(45) Date of Patent: Jul. 19, 2011

(54) ENHANCED DETECTION OF RNA USING A PANEL OF TRUNCATED GENE-SPECIFIC PRIMERS FOR REVERSE TRANSCRIPTION

(75) Inventors: Michael Mitas, Moncks Corner, SC (US); David J. Cole, Mt. Pleasant, SC (US); William E. Gillanders, Charleston, SC (US); Kaidi Mikhitarian, Columbia, MO (US)

(73) Assignee: MUSC Foundation for Research Development, Charleston, SC (US)

( * ) Notice: Subject to any disclaimer, the term of this patent is extended or adjusted under 35 U.S.C. 154(b) by 638 days.

(21) Appl. No.: 10/590,891

(22) PCT Filed: Feb. 25, 2005

(86) PCT No.: PCT/US2005/006292
§ 371 (c)(1),
(2), (4) Date: May 20, 2008

(87) PCT Pub. No.: WO2005/055804
PCT Pub. Date: Jun. 23, 2005

(65) Prior Publication Data
US 2008/0233563 A1    Sep. 25, 2008

Related U.S. Application Data

(60) Provisional application No. 60/548,552, filed on Feb. 27, 2004.

(51) Int. Cl.
*C12Q 1/68* (2006.01)
(52) U.S. Cl. .................................................. 435/6.1
(58) Field of Classification Search .................. None
See application file for complete search history.

(56) References Cited

U.S. PATENT DOCUMENTS

| | | | | |
|---|---|---|---|---|
| 5,314,809 | A | * | 5/1994 | Erlich et al. |
| 5,773,213 | A | * | 6/1998 | Gullans et al. ................. 435/6 |
| 5,801,016 | A | | 9/1998 | Morioka et al. |
| 5,814,491 | A | * | 9/1998 | Vijg et al. |
| 5,837,442 | A | * | 11/1998 | Tsang |
| 5,843,761 | A | * | 12/1998 | Barnett et al. |
| 5,854,033 | A | * | 12/1998 | Lizardi |
| 5,882,856 | A | * | 3/1999 | Shuber |
| 5,958,349 | A | * | 9/1999 | Petersen et al. |
| 6,004,756 | A | * | 12/1999 | Watson et al. |
| 6,037,129 | A | * | 3/2000 | Cole et al. |
| 6,040,138 | A | * | 3/2000 | Lockhart et al. |
| 6,057,105 | A | * | 5/2000 | Hoon et al. |
| 6,183,960 | B1 | * | 2/2001 | Lizardi |
| 6,210,884 | B1 | * | 4/2001 | Lizardi |
| 6,245,517 | B1 | * | 6/2001 | Chen et al. |
| 6,251,601 | B1 | * | 6/2001 | Bao et al. |
| 6,261,776 | B1 | * | 7/2001 | Pirrung et al. |
| 6,306,643 | B1 | * | 10/2001 | Gentalen et al. |
| 6,309,823 | B1 | * | 10/2001 | Cronin et al. |
| 6,344,329 | B1 | * | 2/2002 | Lizardi |
| 6,346,413 | B1 | * | 2/2002 | Fodor et al. |
| 6,374,684 | B1 | * | 4/2002 | Dority et al. |
| 6,403,037 | B1 | * | 6/2002 | Chang et al. |
| 6,406,844 | B1 | | 6/2002 | Pirrung et al. |
| 6,416,952 | B1 | | 7/2002 | Pirrung et al. |
| 6,431,476 | B1 | | 8/2002 | Taylor et al. |
| 6,440,725 | B1 | | 8/2002 | Pourahmadi et al. |
| 7,101,663 | B2 | | 9/2006 | Godfrey et al. |
| 7,824,857 | B2 | | 11/2010 | Mitas et al. |

FOREIGN PATENT DOCUMENTS

| | | |
|---|---|---|
| EP | 1 050 587 | 11/2000 |
| WO | WO 98/08970 | 8/1990 |
| WO | WO 95/11687 | 5/1995 |
| WO | WO 99/13104 | 3/1999 |
| WO | WO 00/44774 | 8/2000 |
| WO | WO 00/72970 | 12/2000 |
| WO | WO 00/73412 | 12/2000 |
| WO | WO 00/73413 | 12/2000 |
| WO | WO 01/01129 | 1/2001 |
| WO | WO 01/45845 | 6/2001 |
| WO | WO 01/57253 | 8/2001 |
| WO | WO 01/84463 | 11/2001 |
| WO | WO 02/18902 | 3/2002 |
| WO | WO 02/052030 | 7/2002 |
| WO | WO 02/070751 | 9/2002 |
| WO | WO 03/055973 | 12/2002 |
| WO | WO 03/072253 | 9/2003 |
| WO | WO 03/077055 | 9/2003 |
| WO | WO 2004/048931 | 6/2004 |

OTHER PUBLICATIONS

Schwarz et al. (J Virol Methods. Feb. 1995;51(2-3):349-56).*
Cerveira et al. (Br J Haematol. Jun. 2000;109(3):638-40).*
Mitas et al. (Br J Cancer. Mar. 18, 2002;86(6):899-904).*
Baker, MK, et al., "Molecular detection of breast cancer cells in the peripheral blood of advanced-stage breast cancer patients using multimarker real-time reverse transcription-polymerase chain reaction and a novel porous barrier density gradient centrifugation technology," *Clin Cancer Res* 9:4865-4871 (2003).
Bieche, I, et al., "Novel approach to quantitative polymerase chain reaction using real-time detection: application to the detection of gene amplification in breast cancer," *Int J Cancer*, 78:661-666 (1998).
Bingle, CD, et al., Characterisation of the human *plunc* gene, a gene product with an upper airways and nasopharyngeal restricted expression pattern, *Biochim Biophys Acta*, 1493:363-367 (2000).
Coombs, NJ, et al., "Optimisation of DNA and RNA extraction from archival formalin-fixed tissue," *Nucleic Acids Res* 27:e12 (i-iii) (1999).
Corey, E, et al., "Detecticn of disseminated prostate cells by reverse transcription-polymerase chain reaction (RT-PCR): technical and clinical aspects," *Int J Cancer* 77:655-673 (1998).

(Continued)

*Primary Examiner* — Christopher M. Babic
(74) *Attorney, Agent, or Firm* — Ballard Spahr LLP

(57) ABSTRACT

The present invention provides truncated gene-specific primers in panels that can be used during the reverse transcription step of RT-PCR to increase signal detection of cancer gene markers in a tissue sample. Also provided are forward and reverse primers for RT-PCR. Methods of using the primers are also provided.

12 Claims, 3 Drawing Sheets

OTHER PUBLICATIONS

Czygan, M., et al., "Borna disease virus in human brains with a rare form of hippocampal degeneration but not in brains of patients with common neuropsychiatric disorders," *J Infec Dis*, 180(5):1695-1699 (1999).

Database Genbank, National Center for Biotechnology Information NLM, N IH; Accession No. AJ246858.1 (1999).

Dennis, P, et al., "Monitoring gene expression in mixed microbial communities by using DNA microarrays," *Appl Environ Microbiol* 69:769-778 (2003).

Ghadersohi A, et al., "Prostate Epithelium-derived Ets Transcription Factor mRNA Is Overexpressed in Human Breast Tumors and Is a Candidate Breast Tumor Marker and a Breast Tumor Antigen," *Clin Cancer Res*, 7:2731-2738 (2001).

Godfrey, TE, et al., "Quantitative mRNA expression analysis from formalin-fixed, paraffin-embedded tissues using 5' nuclease quantitative reverse transcription-polymerase chain reaction," *J Mol Diagn* 2:84-91 (2000).

Goldsworthy, SM, et al., "Effects of fixation on RNA extraction and amplification from laser capture microdissected tissue," *Mol Carcinog* 25:86-91 (1999).

Körbler, T, et al., "A simple method for RNA isolation from formalin-fixed and paraffin-embedded lymphatic tissues," *Exp Mol Pathol* 74:336-340 (2003).

Masuda, N, et al., "Analysis of chemical modification of RNA from formalin-fixed samples and optimization of molecular biology applications for such samples," *Nucleic Acids Res* 27:4436-4443 (1999).

Mitas, M, et al., "*Lunx* is a superior molecular marker for detection of non-small lung cell cancer in peripheral blood," *J Mol Diagn* 5:237-242 (2003).

Mitas, M, et al., "Prostate-Specific Ets (PSE) factor: a novel marker for detection of metastatic breast cancer in axillary lymph nodes," *Br J Cancer* 86:899-904 (2002).

Mitas, M, et al., "Quantitative real-time RT-PCR detection of breast cancer micrometastasis using a multigene marker panel," *Int J Cancer* 93:162-171 (2001).

Mitas, M, et al., "Real-time reverse transcription-PCR detects *KS1/4* mRNA in mediastinal lymph nodes from patients with non-small cell lung cancer," *Clin Chem* 49:312-315 (2003).

Muller, PY, et al., "Processing of gene expression data generated by quantitative real-time RT-PCR," *Biotechniques*, 32:1372-1374, 1376, 1378-1379 (2002).

Oettgen, P, et al., "PDEF, a novel prostate epithelium-specific Ets transcription factor, interacts with the androgen receptor and activates prostate-specific antigen gene expression," *J Biol Chem*, 275:1216-1225 (2000).

Perez, MS, et al., "Isolation and characterization of a cDNA encoding the KS1/4 epithelial carcinoma marker," *J. Immunol*, 142:3662-3667 (1989).

Rosenberg, R, et al., "Comparison of Two Density Gradient Centrifugation Systems for the Enrichment of Disseminated Tumor Cells in Blood," *Cytometry*, 49:150-158 (2002).

Specht, K, et al., "Quantitative gene expression analysis in microdissected archival formalin-fixed and paraffin-embedded tumor tissue," *Am J Pathol* 158:419-429 (2001).

Stanta, G, et al., "RNA extracted from paraffin-embedded human tissues is amenable to analysis by PCR amplification," *Biotechniques* 11:304, 306, 308 (1991).

Sung, YK, et al., "Plunc, a member of the secretory gland protein family, is up-regulated in nasal respiratory epithelium after olfactory bulbectomy," *J Biol Chem*, 277:12762-12769 (2002).

Weston, W, et al., "Differential display identification of *plunc*, a novel gene expressed in embryonic palate, nasal epithelium, and adult lung," *J Biol Chem*, 274:13698-13703 (1999).

"Genecard for protein-coding TACSTD1 GC02P047449: tumor-associated calcium signal," GeneCards, pp. 1-9 (2006).

"Genecard for protein-coding TACSTD1 GC02P047449: tumor-associated calcium signal," GeneCards, pp. 1-6 (2007 update).

"TagMan® One-Step RT-PCR Master Mix Reagents Kit: Protocol," Biosystems, pp. 1-26 (1999).

Abba et al., "Gene Expression Signature of Estrogen Receptor α Status in Breast Cancer," BMC Genomics, 6:37:1-13 2005.

ABI PRISM 7700 Sequence Detection System, User Bulletin #5, "Multiplex PCR with TagMan® VIC Probes," Applied Biosystems, pp. 1-20 (1998; Updated 2001).

Aronow et al., "Microarray Analysis of Trophoblast Differentiation: Gene Expression Reprogramming in Key Gene Function Categories," Physiol. Genomics, 6:105-116, 2001.

Arumugam et al., "S100P Promotes Pancreatic Cancer Growth, Survival, and Invasion," Clin. Cancer Res., 11(15):5356-5364, 2005.

Balzar et al., "The biology of the 17-1A antigen (Ep-CAM)," J. Mol. Med., 77:699-712, 1999.

Banér, et al., "Signal amplification of padlock probes by rolling circle replication," Nucleic Acids Research, 26(22): 5073-5078 (1998).

Barasch et al., "Mesenchymal to Epithelial Conversion in Rat Metanephros Is Induced by LIF," Cell, 99:377-386, 1999.

Barasch, "Genes and Proteins Involved in Mesenchymal to Epithelial Transition," Curr. Opin. Nephrol. Hypertens., 10:429-436, 2001.

Bates et al., "The Epithelial-Mesenchymal Transition (EMT) and Colorectal Cancer Progression," Cancer Biol. Ther., 4:365-370, 2005.

Bercovich et al., "Quantitative Ratio of Primer Pairs and Annealing Temperature Affecting PCR Products in Duplex Amplification," BioTechniques, 27(4): 762-770 (1999).

Berger et al., "Evaluation of Three mRNA Markers for the Detection of Lymph Node Metastases," Anticancer Res, 26:3855-3860, 2006.

Bosma et al., "Detection of circulating breast tumor cells by differential expression of marker genes," Clin Cancer Res., 8(6):1871-1871, 2001.

Bostic et al., "Limitations of Specific Reverse-Transcriptase Polymerase Chain Reaction Markers in the Detection of Metastases in the Lymph Nodes and Blood of Breast Cancer Patients," J. Clin. Oncol., 16(8): 2632-2640 (1998).

Braun et al. "Exponential DNA Replication by Laminar Convection," Physical Review Letters, 91(15): 158103-1-158103-4 (2003).

Brink et al., "Nucleic Acid Sequence-Based Amplification, a New Method for Analysis of Spliced and Unspliced [EBV] . . . ," J. Clin. Microbio., 36(11): 3164-3169 (1998).

Buck et al., "Design Strategies and Performance of Custom DNA Sequencing Primers," BioTechniques, 27(3): 528-536 (1999).

Canter et al., "On-Chip Amplification of Genomic DNA with Short Tandem Repeat and Single Nucleotide Polymorphism Analysis," Genetic Identity Conference Proceedings Eleventh International Symposium on Human Identification, Nanogen, Inc., San Diego, CA, 14 pages, 2000.

Cappelletti et al., "Prognostic Relevance of pS2 Status in Association With Steroid Receptor Status and Proliferative Activity in Node-negative Breast Cancer," Eur. J. Cancer 28A, No. 8/9:1315-1318, 1992.

Cardoso et al., "Potential Predictive Value of Bcl-2 for Response to Tamoxifen in the Adjuvant Setting of Node-Positive Breast Cancer," Clin. Breast Cancer, vol. 5:364-369, 2004.

Cerfolio et al., "The Role of FDG-PET Scan in Staging Patients With Nonsmall Cell Carcinoma," Ann. Thorac. Surg. 76:861-866, 2003.

Chen et al., "Accurate discrimination of pancreatic ductal adenocarcinoma and chronic pancreatitis using multimarker expression data and samples obtained by minimally invasive fine needle aspiration," Int. J. Can., 120: 1511-1517 (2007).

Cheung et al., "Natural variation in human gene expression assessed in lymphoblastoid cells," Nat. Genetics, 33: 422-425 (2003).

Choi et al., "Mediastinoscopy in Patients With Clinical Stage I Non-Small Cell Lung Cancer." Ann. Thorac. Surg. 75:364-366, 2003.

Christian et al., "Detection of DNA point mutations and mRNA expression levels by rolling circle amplification in individual cells," PNAS, 98(25): 14238-14243 (2001).

Corradini et al., "Maspin and Mammaglobin Genes Are Specific Markers for Rt-PCR Detection of Minimal Residual Disease in Patients With Breast Cancer," Ann Oncol, 12:1693-1698, 2001.

Cote et al., "Role of Immunohistochemical Detection of Lymph-Node Metastases in Management of Breast Cancer," Lancet, vol. 354:896-900, 1999.

Coughlin et al., "Role of Mediastinoscopy in Pretreatment Staging of Patients with Primary Lung Cancer," Ann. Thorac. Surg. vol. 40, No. 6:556-560, 1985.

Czygan et al., "Borna disease virus in human brains with a rare form of hippocampal degeneration but not in brains of patients with common neuropsychiatric disorders," J Infect Dis. 180(5): 1695-1699, 1999.

D'Cunha et al., "Molecular staging of lung cancer: Real-time polymerase chain reaction estimation of lymph node micrometastatic tumor cell burden in stage I non-small cell lung cancer—Preliminary results of Cancer and Leukemia Group B Trial 9761," J. Thor. Cardiov. Surg., 123(3): 484-491 (2002).

de Mascarel et al., "Prognostic Significance of Breast Cancer Axillary Lymph Node Micrometastases Assessed by Two Special Techniques: Reevaluation With Longer Follow-Up," Br. J. Cancer, 66(3):523-527, 1992.

DeBaar et al., "One-Tube Real-Time Isothermal Amplification Assay to Identify and Distinguish [HIV] Type 1 Subtypes . . . ," J. Clin. Microbiol., 39(5): 1895-1902 (2001).

DeBaar et al., "Single Rapid Real-Time Monitored Isothermal RNA Amplification Assay for Quantification of (HIV) Type 1 . . . ," J. Clin. Microbiol., 39(4): 1378-1384 (2001).

Demidov "Rolling-circle amplication in DNA diagnostics: the power of simplicity," Expert Rev. Mol. Diagn., 2(6): 89-95 (2002).

Dessau et al., "Coronaviruses in spinal fluid of patients with acute monosymptomatic optic neuritis," Acta. Neurol. Scand., 100: 88-91 (1999).

Efron et al., "An Introduction to the Bootstrap," Chapman and Hall, pp. 247-252 (1993).

Endoh et al., "Prognostic Model of Pulmonary Adenocarcinoma by Expression Profiling of Eight Genes As Determined by Quantitative Real-Time Reverse Transcriptase Polymerase Chain Reaction," J. Clin. Oncol. vol. 22, No. 5:811-819, 2004.

Esworthy et al., "Epithelium-Specific Glutathione Peroxidase, Gpx2, Is Involved in the Prevention of Intestinal Inflammation in Selenium-Deficient Mice," J. Nutr., 135:740-745, 2005.

Fisher et al., "The Accuracy of Clinical Nodal Staging and of Limited Axillary Dissection as a Determinant of Histologic Nodal Status in Carcinoma of the Breast," Surg. Gynecol. Obstet. 152:765-772, 1981.

Fleming et al., "Mammaglobin, a Breast-Specific Gene, and Its Utility as a Marker for Breast Cancer," Ann N Y Acad Sci, 923: 78-89, 2000.

Fletcher et al., "hAG-2 and hAG-3, Human Homologues of Genes Involved in Differentiation, are Associated With Oestrogen Receptor-Positive Breast Tumours and Interact With Metastasis Gene C4.4a and Dystroglycan," Br. J. Cancer 88:579-585, 2003.

Foekens et al., "Prediction of Relapse and Survival in Breast Cancer Patients by pS2 Protein Status," Cancer Res. 50:3832-3837, 1990.

Foekens et al., "Relationship of PS2 With Response to Tamoxifen Therapy in Patients With Recurrent Breast Cancer," Br. J. Cancer 70:1217-1223, 1994.

Gardner et al., "Are Positive Axillary Nodes in Breast Cancer Markers for Incurable Disease?," Ann. Surg. vol. 218, No. 3:270-278, 1993.

Ge et al., "Detection of Disseminated Lung Cancer Cells in Regional Lymph Nodes by Assay of $CK_{19}$ Reverse Transcriptase Polymerase Chain Reaction and Its Clinical Significance," J Cancer Res. Clin. Oncol. 131:662-668, 2005.

Gillanders et al., "Molecular Detection of Micrometastatic Breast Cancer in Histopathlogy-Negative Axillary Lymph Nodes Correlates with Traditional Predictors of Prognosis," Ann. Surg., 239(6): 828-840, 2004.

Godfrey et al., "Prognostic Value of Quantitative Reverse Transcription-Polymerase Chain Reaction . . . ," Clinical Cancer Research, 7: 4041-4048 (2001).

Gonzalez-Stawinski et al., "A Comparative Analysis of Positron Emission Tomography and Mediastinoscopy in Staging Non-Small Cell Lung Cancer." J. Thorac. Cardiovasc. Surg. 126:1900-1904, 2003.

Greijer et al., "Multiplex real-time NASBA for monitoring expression dynamics of human cytomegalovirus encoded IEI and pp67 RNA," Journal of Clinical Virology, 24: 57-66 (2002).

Grünewald et al., "Mammaglobin Gene Expression: A Superior Marker of Breast Cancer Cells in Peripheral Blood in Comparison to Epidermal-Growth-Factor Receptor and Cytokeratin-19," Lab Invest 80(7):1071-1077, 2000.

Grützmann et al., "Microarray-based Gene Expression Profiling in Pancreatic Ductal Carcinoma: Status Quo and Perspectives," Int J Colorect Dis 19:401-413, 2004.

Gu et al., "Detection of Micrometastatic Tumor Cells in pN0 Lymph Nodes of Patients With Completely Resected Nonsmall Cell Lung Cancer," Ann. Surg.vol. 235, No. 1:133-139, 2002.

Gutierrez et al., "Molecular Changes in Tamoxifen-Resitant Breast Cancer: Relationship Between Estrogen Receptor, HER-2, and p38 Mitogen-Activated Protein Kinase," J. Clin. Oncol. vol. 23, No. 11:2469-2476, 2005.

Harris, et al., "Typing of Dengue Viruses in Clinical Specimens and Mosquitoes by Single-Tube Multiplex Reverse Transcriptase PCR," Jour. Clin. Microbiol., 36(9): 2634-2639 (1998).

Helfrich et al., "A quantitative reverse transcriptase polymerase chain reaction-based assay to detect carcinoma cells in peripheral blood," Br J Cancer, 76(1): 29-35, 1997.

Henderson, "Assessing Test Accuracy and Its Clinical Consequences: A Primer for Receiver Operating Characteristic Curve Analysis," Ann. Clin. Biochem. 30:521-539, 1993.

Henry et al., "pNR-2/pS2 immunohistochemical staining in breast cancer: correlation with prognostic factors and endocrine response," Br. J. Cancer, 63:615-622, 1991.

Hirschhorn et al., "A comprehensive review of genetic association studies," Gen. Med., 4(2): 45-61 (2002).

Hogan et al., "Rap1 Regulates the Formation of E-Cadherin-Based Cell-Cell Contacts," Mol. Cell. Biol., 24(15): 6690-6700, 2004.

Hoshikawa et al., "Hypoxia induces different genes in the lungs of rats compared with mice," Phyisiol. Genomics, 12: 209-219 (2003).

Huber et al., "Molecular Requirements for Epithelial-Mesenchymal Transition During Tumor Progression," Curr. Opin. Cell Biol. 17:548-558, 2005.

International (Ludwig) Breast Cancer Study Group, "Clinical Practice: Prognostic Importance of Occult Axillary Lymph Node Micrometastases From Breast Cancers," The Lancet, 335:1565-1568, 1990.

Ioannidis et al., "Replication validity of genetic association studies," Nat. Genetics, 29: 306-309 (2001).

Janssens et al., "Housekeeping Genes as Internal Standards in Cancer Research," Mol. Diagn. 8:107-113, 2004.

Jiao et al., "Clinical Significance of Micrometastasis in Lung and Esophageal Cancer: A New Paradigm in Thoracic Oncology," Ann. Thorac. Surg., 74: 278-284 (2002).

Kerr et al., "Bootstrapping cluster analysis: Assessing the reliability of conclusions from microarray experiments," PNAS, 98(16): 8961-8965 (2001).

Kettunen et al., "Differentially expressed genes in nonsmall cell lung cancer: expression profiling of cancer-related genes in squamous cell lung cancer," Cancer Genet Cytogenet. 149(2): 98-106, 2004.

Knust et al., "EGF homologous sequences encoded in the genome of *Drosophila melanogaster*, and their relation to neurogenic genes," EMBO J., 6(3):761-766, 1987.

Kobayashi et al., "A Kunitz-type Protease Inhibitor, Bikunin, Inhibits Ovarian Cancer Cell Invasion by Blocking the Calcium-dependent Transforming Growth Factor-β1 Signaling Cascade," J. Biol. Chem. vol. 278, No. 10:7790-7799, 2003.

Krishnan et al., "PCR in Rayleigh-Bénard Convection Cell," Science, 298(5594): 793 (2002).

Kubuschok, et al., "Disseminated Tumor Cells in Lymph Nodes as a Determinant for Survival in Surgically Resected Non-Small-Cell Lung Cancer," Jour. Clin. Oncology, 17(1): 19-24 (1999).

Le Pimpec-Barthes et al., "Association of CK19 mRNA Detection of Occult Cancer Cells in Mediastinal Lymph Nodes in Non-Small Cell Lung Carcinoma and High Risk of Early Recurrence," Eur. J Cancer 41:306-312, 2005.

Leone, et al., "Molecular beacon probes combined with amplification by NASBA enable homogeneous, real-time detection of RNA," Nucleic Acids Research, 26(9): 2150-2155 (1998).

Leygue et al., "Mammaglobin, a potential marker of breast cancer nodal metastasis," J Pathol., 189(1):28-33, 1999.

Levashova et al., "Conditionally Immortalized Cell Line of Inducible Metanephric Mesenchyme," Kidney Int. 63:2075-2087, 2003.

Little, et al., "Molecular Diagnostics and Genetics," Clinical Chemistry, 45(6): 777-784 (1999).

Liu et al., "Mammaglobin mRNA measurement in the detection of micrometastasis in peripheral blood of breast cancer patients," Zhonghua Zhong Liu Za Zhi., 23(4): 317-9, 2001 (Chinese).

Liu et al., "Human Homologue of Cement Gland Protein, a Novel Metastasis Inducer Associated with Breast Carcinomas," Cancer Res. 65 (9):3796-3805, 2005.

Livak et al., "Analysis of Relative Gene Expression Data Using Real-time Quantitative PCR and the $2^{-\Delta\Delta C_T}$ Method," Methods 25:402-408, 2001.

Lockley et al., "Colormetric detection of immobilised PCR products generated on a solid support," Nucleic Acids Research, 25(6): 1313-1314 (1997).

Luketich et al., "Detection of Micrometastases in Histologically Negative Lymph Nodes in Esophageal Cancer," Ann. Thorac. Surg., 66: 1715-1718 (1998).

Manni et al., "Estrogen and Progesterone Receptors in the Prediction of Response of Breast Cancer to Endocrine Therapy," Cancer 46:2838-2841, 1980.

Marazuela et al., "Expression of MAL2, an Integral Protein Component of the Machinery for Basolateral-to-Apical Transcytosis, in Human Epithelia," J. Histochem. Cytochem. 52:243-252, 2004.

Marchetti et al., "mRNA Markers of Breast Cancer Nodal Metastases: Comparison Between Mammaglobin and Carcinoembryonic Antigen in 248 Patients," J. Pathol 195(2):186-190, 2001.

Matsuda et al., "Significance of Metastasis Detected by Molecular Techniques in Sentinel Nodes of Patients with Gastrointestinal Cancer," Annals of Surgical Oncology, 11(3): 250S-254S (2004).

McGuckin et al., "Occult Axillary Node Metastases in Breast Caccer: Their Detection and Prognostic Significance," Br. J. Cancer 73:88-95, 1996.

McGuire et al., "Current Status of Estrogen and Progesterone Receptors in Breast Cancer," Cancer 39:2934-2947, 1977.

McLaughlin et al., "The epithelial glycoprotein 2 (EGP-2) promoter-driven epithelial-specific expression of EGP-2 in transgenic mice: a new model to study carcinoma-directed immunotherapy," Cancer. Res., 61(10): 4105-4011.

Meng et al., "Human ADA3 Binds to Estrogen Receptor (ER) and Functions As a Coactivator for ER-mediated Transactivation," J. Biol. Chem., 279(52): 54230-54240, 2004.

Mikhitarian, et al., "An Innovative Microarray Strategy Identifies Informative Molecular Markers for the Detection of Micrometastatic Breast Cancer," Clin. Cancer Res., 11(10): 3697-3704 (2005).

Mikhitarian et al., "Enhanced detection of RNA from paraffin-embedded tissue using a panel of truncated gene-specific primers for reverse transcription," BioTechniques, 36(3): 474-477 (2004).

Min et al., "Identification of Superior Markers for Polymerase Chain Reaction Detection of Breast Cancer Metastases in Sentinel Lymph Nodes," Cancer Res. 58:4581-4584, 1998.

Mitas et al., "Prostate-Specific Ets (PSE) factor: A Novel Marker for Detection of Metastatic Breast Cancer in Axillary Lymph Nodes," British Journal of Cancer 86:899-904, 2002.

Mitas et al., "Quantitative Real-Time RT-PCR Detection of Breast Cancer Micrometastasis Using a Multigene Marker Panel," Int. J. Cancer, 93: 162-171 (2001).

Mitas et al., "Accurate Discrimination of Barrett's Esophagus and Esophageal Adenocarcinoma Using a Quantitative Three-Tiered Algorithm and Multi-Marker Real-time Reverse Transcription-PCR," Clin. Can. Res., 11: 2205-2214 (2005).

Mitas et al., "Lunx is a Superior Molecular Marker for Detection of Non-Small Lung Cell Cancer in Peripheral Blood," J. Mol. Diag., 5(4): 237-242 (2003).

Mitas et al., "Real-Time Reverse Transcription-PCR Detects KS1/4 mRNA in Mediastinal Lymph Nodes from Patients with Non-Small Cell Lung Cancer," Clin. Chem., 49(2): 312-315 (2003).

Miyake et al., "Quantification of micrometastases in lymph nodes of colorectal cancer using real-time fluorescence polymerase chain reaction," Int. J. Oncol., 16(2): 289-293 (2000).

Mondesire et al., "Solid-phase nucleic acid extraction, amplification, and detection," IVD Technology Magazine (2000).

Morrison et al., "Quantification of Low-Copy Transcripts by Continuous SYBR® Green I Monitoring during Amplification," BioTechniques, 24(60): 954-962 (1998).

Nagaraju et al., "FISSR-PCR: a simple and sensitive assay for highthroughput genotyping and genetic mapping," Molecular and Cellular Probes, 16: 67-72 (2002).

Nakanishi et al., "Rapid Quantitative Detection of Carcinoembryonic Antigen-Expressing Free Tumor Cells in the Peritoneal Cavity of Gastric-Cancer Patients with Real-Time-PCR on the Lightcycler," Int. J. Cancer (Pred. Oncol.), 89: 411-417 (2000).

Nallur et al., "Signal amplification by rolling circle amplification on DNA microarrays," Nucleic Acids Research, 29(23) e118, pp. 1-9 (2001).

NCBI Accession NM_000213, ITGB4, The NCBI handbook [Internet]. Bethesda (MD): Natl Lib Med (US), 2002, Ch.18 The RefSeq Project.

NCBI Accession NM_000224, CK18, The NCBI handbook [Internet]. Bethesda (MD): Natl Lib Med (US), 2002, Ch.18 The.

NCBI Accession NM_000245, c-MET, The NCBI handbook [Internet]. Bethesda (MD): Natl Lib Med (US), 2002, Ch.18 The RefSeq Project.

NCBI Accession NM_000372, TYR, The NCBI handbook [Internet]. Bethesda (MD): Natl Lib Med (US), 2002, Ch.18 The RefSeq Project.

NCBI Accession NM_000453, NIS, The NCBI handbook [Internet]. Bethesda (MD): Natl Lib Med (US), 2002, Ch.18 The RefSeq Project.

NCBI Accession NM_000526, CK14, The NCBI handbook [Internet]. Bethesda (MD): Natl Lib Med (US), 2002, Ch.18 The RefSeq Project.

NCBI Accession NM_000542, SFTPB, The NCBI handbook [Internet]. Bethesda (MD): Natl Lib Med (US), 2002, Ch.18 The RefSeq Project.

NCBI Accession NM_000737, BHCG, The NCBI handbook [Internet]. Bethesda (MD): Natl Lib Med (US), 2002, Ch.18 The RefSeq Project.

NCBI Accession NM_001168, Survivin, The NCBI handbook [Internet]. Bethesda (MD): Nati Lib Med (US), 2002, Ch.18 The RefSeq Project.

NCBI Accession NM_001169, SSXu, The NCBI handbook [Internet]. Bethesda (MD): Natl Lib Med (US), 2002, Ch.18 The RefSeq Project.

NCBI Accession NM_001187, BAGE, The NCBI handbook [Internet]. Bethesda (MD): Natl Lib Med (US), 2002, Ch.18 The RefSeq Project.

NCBI Accession NM_001327, CTAG1, The NCBI handbook [Internet]. Bethesda (MD): Natl Lib Med (US), 2002, Ch.18 The RefSeq Project.

NCBI Accession NM_001468, GAGE1, The NCBI handbook [Internet]. Bethesda (MD): Natl Lib Med (US), 2002, Ch.18 The RefSeq Project.

NCBI Accession NM_001726, BRDT, The NCBI handbook [Internet]. Bethesda (MD): Natl Lib Med (US), 2002, Ch.18 The RefSeq Project.

NCBI Accession NM_001944, PVA, The NCBI handbook [Internet]. Bethesda (MD): Natl Lib Med (US), 2002, Ch.18 The RefSeq Project.

NCBI Accession NM_002276, CK19 The NCBI handbook (Internet). Bethesda (MD): Natl Lib Med (US), 2002, Ch.18 The RefSeq Project.

NCBI Accession NM_002281, KRTHBI, The NCBI handbook (Internet). Bethesda (MD): Natl Lib Med (US), 2002, Ch.18 The RefSeq Project.

NCBI Accession NM_002354, TACSTDI, The NCBI handbook (Internet). Bethesda (MD): Natl Lib Med (US), 2002, Ch.18 The RefSeq Project.

NCBI Accession NM_002362, MAGEA4, The NCBI handbook [Internet]. Bethesda (MD): Natl Lib Med (US) 2002, Ch.18 The RefSeq Project.

NCBI Accession NM_002407, The NCBI handbook [Internet]. Bethesda (MD): Natl Lib Med (US), 2002, Ch.18 The RefSeq Project.
NCBI Accession NM_002411, The NCBI handbook (Internet). Bethesda (MD): Natl Lib Med. (US), 2002, Ch.18 The RefSeq Project.
NCBI Accession NM_002423, MMP7, The NCBI handbook [Internet). Bethesda (MD): Natl Lib Med (US), 2002, Ch.18 The RefSeq Project.
NCBI Accession NM_002652, PIP, The NCBI handbook [Internet]. Bethesda (MD): Natl Lib Med (US), 2002, Ch.18 The RefSeq Project.
NCBI Accession NM_002820, PTHrP, The NCBI handbook [Internet]. Bethesda (MD): Natl Lib Med (US), 2002, Ch.18 The RefSeq Project.
NCBI Accession NM_002974, SCCA2, The NCBI handbook [Internet]. Bethesda (MD): Natl Lib Med (US), 2002, Ch.18 The RefSeq Project.
NCBI Accession NM_003219, HTERT, The NCBI handbook [Internet). Bethesda (MD): Natl Lib Med (US), 2002, Ch.18 The RefSeq Project.
NCBI Accession NM_003317, TITF1, The NCBI handbook [Internet]. Bethesda (MD): Natl Lib Med (US), 2002, Ch.18 The RefSeq Project.
NCBI Accession NM_004363, CEA, The NCBI handbook [Internet]. Bethesda (MD): Natl Lib Med (US), 2002, Ch.18 The RefSeq Project.
NCBI Accession NM_004616, TM4SF3. The NCBI handbook (Internet). Bethesda (MD): Natl Lib Med (US). 2002, Ch.18 The RefSeq Project.
NCBI Accession NM_004988, MAGEA1, The NCBI handbook (Internet). Bethesda (MD): Natl Lib Med (US), 2002, Ch.18 The RefSeq Project.
NCBI Accession NM_005361, MAGEA2, The NCBI handbook (Internet). Bethesda (MD): Natl Lib Med (US) 2002, Ch.18 The RefSeq Project.
NCBI Accession NM_005362, MAGEA3, The NCBI handbook (Internet). Bethesda (MD): Natl Lib Med (US), 2002, Ch.18 The RefSeqProject.
NCBI Accession NM_005364, MAGEAB, The NCBI handbook [Internet]. Bethesda (MD): Natl Lib Med (US) 2002, Ch.18 Rhe RefSeq Project.
NCBI Accession NM_005367, MAGEA12, The NCBI handbook [Internet). Bethesda (MD): Natl Lib Med (US), 2002, Ch.18 The RefSeq Project.
NCBI Accession NM_005556, CK7, The NCBI handbook [Internet]. Bethesda (MD): Natl Lib Med (US), 2002, Ch.18 The RefSeq Project.
NCBI Accession NM_006011, SSX2, The NCBI handbook [Internet]. Bethesda (MD): Natl Lib Med (US), 2002, Ch.18 The RefSeq Project.
NCBI Accession NM_006183, NTS, The NCBI handbook (Internet). Bethesda (MD): Natl Lib Med (US), 2002, Ch.18 The RefSeq Project.
NCBI Accession NM_006919, SCCA1, The NCBI handbook [Internet]. Bethesda (MD): Natl Lib Med (US), 2002, Ch.18 The RefSeq Project.
NCBI Accession NM_007127, Viilin 1, The NCBI handbook [Internet]. Bethesda (MD): Natl Lib Med (US), 2002, Ch.18 The RefSeq Project.
NCBI Accession NM_014419, SGY-1, The NCBI handbook [Internet]. Bethesda (MD): Natl Lib Med (US), 2002, Ch.18 The RefSeq Project.
NCBI Accession NM_017448, LUNX, The NCBI handbook (Internet). Bethesda (MD): Natl Lib Med (US), 2002, Ch.18 The RefSeq Project.
NCBI Accession NM_019010, CK20 The NCBI handbook [Internet). Bethesda (MD): Natl Lib Med (US), 2002, Ch.18 The RefSeq Project.
NCBI Accession NM_021048, MAGEA10, The NCBI handbook [Internet]. Bethesda (MD): Natl Lib Med (US), 2002, Ch.18 The RefSeq Project.

NCBI Accession NM_130852, LDHC, The NCBI handbook [Internet]. Bethesda (MD): Natl Lib Med (US), 2002, Ch.18 The RefSeq Project.
Nilsson et al., "Making Ends Meet in Genetic Analysis Using Padlock Probes," Human Mutation, 19: 410-415 (2002).
Nissan et al.,"Multimarker RT-PCR Assay for the Detection of Minimal Residual Disease in Sentinel Lymph Nodes of Breast Cancer Patients," Br J Cancer 94:681-685, 2006.
Oehlenschläger, et al., "Detection of HIV-1 RNA by nucleic acid sequence-based amplification combined with fluorescence correlation spectroscopy," PNAS, 93: 12811-12816 (1996).
Ohta et al., "Can Tumor Size Be a Guide for Limited Surgical Intervention in Patients With Peripheral Non-Small Cell Lung Cancer? Assessment From the Point of View of Nodal Micrometastasis," J. Thorac. Cardiovasc. Surg. 122:900-906, 2001.
Okada et al., "Effect of Tumor Size on Prognosis in Patients With Non-Small Cell Lung Cancer: The Role of Segmentectomy as a Type Lesser Resection," J. Thorac. Cardiovasc. Surg. 129:87-93, 2005.
Osaki et al., "Prognostic Impact of Micrometastatic Tumor Cells in the Lymph Nodes and Bone Marrow of Patients With Completely Resected Stage I Non-Small-Cell Lung Cancer," J. Clin. Oncol. 20: 2930-2936, 2002.
Oshima, et al., "Cloning, sequencing, and expression of cDNA for human β-glucuronidase," PNAS USA, 84: 685-689 (1987).
Osta et al., "EpCAM is Overexpressed in Breast Cancer and is a Potential Target for Breast Cancer Gene Therapy," Cancer Research, 64: 5818-5824 (2004).
Ouellette et al., "RT-PCR for Mammaglobin Genes, MGB1 and MGB2, Identifies Breast Cancer Micrometastases in Sentinel Lymph Nodes," Am J Clin Pathol, 121(5):637-643, 2004.
Paik et al., "A Multigene Assay to Predict Recurrence of Tamoxifen-Treated, Node-Negative Breast Cancer," N. Engl. J. Med. 351:2817-2826, 2004.
Patterson et al., "A Prospective Evaluation of Magnetic Resonance Imaging, Computed Tomography, and Mediastinoscopy in the Preoperative Assessment of Mediastinal Node Status in Bronchogenic Carcinoma," J. Thorac. Cardiovasc. Surg. 94:679-684, 1987.
Patz et al., "Thoracic Nodal Staging With PET Imaging With 18FDG in Patients With Bronchogenic Carcinoma," Chest 108:1617-1621, 1995.
Perez et al., "Isolation and characterization of a cDNA encoding the KS1/4 epithelial carcinoma marker," J. Immunology, 142: 3662-3667, 1989.
Petek et al., "Localization of the Human Anterior Gradient-2 Gene (AGR2) to Chromosome Band 7p21.3 by Radiation Hybrid Mapping and Fluorescence in Situ Hybridisation," Cytogenet. Cell Genet. 89:141-142, 2000.
Petz et al., "Differential Regulation of the Human Progesterone Receptor Gene Through an Estrogen Response Element Half Site and Spl Sites," J. Steroid Biochem. Mol. Biol. 88:113-122, 2004.
Pohler et al., "The Barrett's Antigen Anterior Gradient-2 Silences the p53 Transcriptional Response to DNA Damage" Mol. Cell Proteomics 3:534-547, 2004.
Raja et al., "Increased Sensitivity of One-Tube, Quantitative RT-PCR," BioTechniques, 29(4): 702-706 (2000).
Raja et al., "Rapid, quantitative reverse transcriptase-polymerase chain reaction: Application to intraoperative molecular detection of occult metastases in esophageal cancer," J. Thor. Card. Surg., 123(3): 475-483 (2002).
Ribieras et al., "The pS2/TFF1 Trefoil Factor, From Basic Research to Clinical Applications," Biochim. Biophys. Acta 1378:F61-F77, 1998.
Rio et al., "Specific Expression of the Ps2 Gene in Subclasses of Breast Cancers in Comparison With Expression of the Estrogen and Progesterone Receptors and the Oncogene ERBB2," Proc. Natl. Acad. Sci. USA 84:9243-9247, 1987.
Roberts et al., "Interpretive disparity among pathologists in breast sentinel lymph node evaluation," Am. J. Surg., 186: 324-329 (2003).
Saimura et al., "Prognosis of a Series of 763 Consecutive Node-Negative Invasive Breast Cancer Patients Without Adjuvant Therapy: Analysis of Clinicopathological Prognostic Factor," J Surg. Oncol. 71: p. 101-105, 1999.

Sakaguchi et al., "Clinical Relevance of Reverse Transcriptase-Polymerase Chain Reaction for the Detection of Axillary Lymph Node Metastases in Breast Cancer," Annals of Surg. Oncol., 10(2): 117-125 (2003).

Schena et al., "Parallel Human Genome Analysis: Microarray-Based Expression Monitoring of 1000 Genes," Proc. Natl. Acad. Sci. USA 93:10614-10619, 1996.

Schmittgen et al., "Quantitative Reverse Transcription-Polymerse Chain Reaction to Study mRNA Decay: Comparison of Endpoint and Real-Time Methods," Anal. Biochem. 285:194-204, 2000.

Schröder et al., "Detection of Micrometastatic Breast Cancer by Means of Real Time Quantitative RT-PCR and Immunostaining in Perioperative Blood Samples and Sentinel Nodes," Int. J. Cancer, 106: 611-618 (2003).

Schultz et al., "Estrogen Receptor α and Sp1 Regulate Progesterone Receptor Gene Expression," Mol. Cell Endocrinol. 201:165-175, 2003.

Schweitzer et al., "Combining nucleic acid amplification and detection," Curr. Opin. Biotechnol., 12: 21-27 (2001).

Schweitzer et al., "Immunoassays with rolling circle DNA amplification: A versatile platform for ultrasensitive antigen detection," PNAS, 97(18): 10113-10119 (2000).

Seshadri et al., "The Relative Prognostic Significance of Total Cathepsin D and Her-2/neu Oncogene Amplification in Breast Cancer," Int. J. Cancer, 56: 61-65, 1994.

Silva et al., "Detection of epithelial tumour RNA in the plasma of colon cancer patients is associated with advanced stages and circulating tumour cells," Gut., 50: 530-534 (2002).

Sjödin et al., "Dysregulated secretoglobin expression in human lung cancers," Lung Cancer, 41:49-56, 2003.

Smid et al., "Genes Associated With Breast Cancer Metastatic to Bone," J Clin Oncol, 24(15):2261-2267, 2006.

Smirnov et al., "Global Gene Expression Profiling of Circulating Tumor Cells," Cancer Res. 65:4993-4997, 2005.

Specht et al., "Quantitative Gene Expression Analysis in Microdissected Archival Formalin-Fixed and Paraffin-Embedded Tumor Tissue," Am. J. Pathol. 158:419-429, 2001.

Spruance et al., "Hazard Ratio in Clinical Trials," Antimicrob. Agents & Chemo. 48(8):2787-2792, 2004.

Strauss et al., "Randomized Clinical Trial of adjuvant chemotherapy with paclitaxel and carboplatin following resection in Stage IB Non-Small Cell Lung Cancer (NSCLC): Report of Cancer and Leukemia Group B (CALGB) Protocol 9633," J. Clin. Oncol. 22(14S): 7019, 2004 (.

Sun et al., "Estrogen regulation of trefoil factor 1 expression by estrogen receptor α and Sp proteins," Exp. Cell Res. 302:96-107, 2005.

Thomas et al., "Amplification of Padlock Probes for DNA Diagnostics by Cascade Rolling Circle Amplification or the Polymerase Chain Reaction," Arch. Pathol. Lab Med., 123: 1170-1176 (1999).

Thompson et al., "hAG-2, the Human Homologue of the *Xenopus laevis* Cement Gland Gene XAG-2, Is Coexpressed with Estrogen Receptor in Breast Cancer Cell Lines," Biochem. Biophys. Res. Commun. 251:111-116, 1998.

Tockman et al., Considerations in bringing a cancer biomarker to clinical application, Cancer Res., 52(9 Suppl):2711s-2718s, 1992.

Troutt et al., "Ligation-anchored PCR: A simple amplification technique with single-sided specificity," PNAS USA, 89: 9823-9825 (1992).

Varki et al., "Antigens associated with a human lung adenocarcinoma defined by monoclonal antibodies," Cancer Research, 1984, 44(2)681-687.

Viehmann et al., "Multiplex PCR—a rapid screening method for detection of gene rearrangements in childhood acute lymphoblastic leukemia," Annals of Hematol., 78: 157-162 (1999).

Wallace et al., "Accurate Molecular Detection of Non-small Cell Lung Cancer Metastases in Mediastinal Lymph Nodes Sampled by Endoscopic Ultrasound-Guided Fine Needle Aspiration," Chest, 127(2): 430-437 (2005).

Watson et al., "Mammaglobin, a Mammary-specific Member of the Uteroglobin Gene Family, Is Overexpressed in Human Breast Cancer," Cancer Res. 56:860-865, 1996.

Watson et al., "Mammaglobin Expression in Primary, Metastatic, and Occult Breast Cancer," Cancer Res 59(13):3028-3031, 1999.

Weigelt et al., "Detection of Metastases in Sentinel Lymph Nodes of Breast Cancer Patients by Multiple mRNA Markers," Br J Cancer 90(8):1531-1537, 2004.

Winton et al., "Vinorelbine plus Cisplatin vs. Observation in Resected Non-Small-Cell Lung Cancer," N. Engl. J. Med. 352:2589-2597, 2005.

Wisnivesky et al., "The Effect of Tumor Size on Curability of Stage I Non-small Cell Lung Cancers," Chest 126: p. 761-765, 2004.

Wu et al., "Nodal Occult Metastasis in Patients With Peripheral Lung Adenocarcinoma of 2.0 cm or Less in Diameter," Ann. Thorac. Surg. 71:1772-1778, 2001.

Wu et al., "The Effect of Temperature and Oligonucleotide Primer Length on the Specificity and Efficiency of Amplification by Polymerase Chain Reaction," DNA and Cell Biology, 10(3): 233-238 (1991).

Yang et al., "Twist, a Master Regulator of Morphogenesis, Plays an Essential Role in Tumor Metastasis," Cell 117:927-939, 2004.

Ylitalo et al., "Detection of Genital Human Papillomavirus by Single-Tube Nested PCR and Type-Specific Oligonucleotide Hybridization," Jour. Clin. Microb., pp. 1822-1828 (1995).

Zach et al., "Statistical Validation of the Mammaglobin-Nested RT-PCR Assay for Tumor Cell Detection in Blood of Breast Cancer Patients," Biotechniques 31(6):1358-1362, 2001.

Zheng et al., "Variation of ER status between primary and metastatic breast cancer and relationship to p53 expression," Steroids 66:905-910, 2001.

Issue Notification issued Oct. 13, 2010 for U.S. Appl. No. 11/003,223, filed Dec. 2, 2004 and issued as U.S. Pat. No. 7,824,857 on Nov. 2, 2010 (Inventors: Mitas et al.).

Notice of Allowance issued Jul. 26, 2010 for U.S. Appl. No. 11/003,223, filed Dec. 2, 2004 and issued as U.S. Pat. No. 7,824,857 on Nov. 2, 2010 (Inventors: Mitas et al.).

Amendment and Response to Office Action filed Jun. 25, 2010 for U.S. Appl. No. 11/003,223, filed Dec. 2, 2004 and issued as U.S. Pat. No. 7,824,857 on Nov. 2, 2010 (Inventors: Mitas et al.).

Non-Final Rejection issued Apr. 15, 2010 for U.S. Appl. No. 11/003,223, filed Dec. 2, 2004 and issued as U.S. Pat. No. 7,824,857 on Nov. 2, 2010 (Inventors: Mitas et al.).

Amendment and Response to Office Action filed Feb. 23, 2010 for U.S. Appl. No. 11/003,223, filed Dec. 2, 2004 and issued as U.S. Pat. No. 7,824,857 on Nov. 2, 2010 (Inventors: Mitas et al.).

Notice of Non-Compliant Amendment issued Jan. 28, 2010 for U.S. Appl. No. 11/003,223, filed Dec. 2, 2004 and issued as U.S. Pat. No. 7,824,857 on Nov. 2, 2010 (Inventors: Mitas et al.).

Amendment and Response to Office Action filed Sep. 1, 2009 for U.S. Appl. No. 11/003,223, filed Dec. 2, 2004 and issued as U.S. Pat. No. 7,824,857 on Nov. 2, 2010 (Inventors: Mitas et al.).

Final Rejection issued May 14, 2009 for U.S. Appl. No. 11/003,223, filed Dec. 2, 2004 and issued as U.S. Pat. No. 7,824,857 on Nov. 2, 2010 (Inventors: Mitas et al.).

Amendment and Response to Office Action filed Mar. 24, 2009 for U.S. Appl. No. 11/003,223, filed Dec. 2, 2004 and issued as U.S. Pat. No. 7,824,857 on Nov. 2, 2010 (Inventors: Mitas et al.).

Non-Final Action issued Sep. 26, 2008 for U.S. Appl. No. 11/003,223, filed Dec. 2, 2004 and issued as U.S. Pat. No. 7,824,857 on Nov. 2, 2010 (Inventors: Mitas et al.).

Decision on Petition issued Jul. 25, 2008 for U.S. Appl. No. 11/003,223, filed Dec. 2, 2004 and issued as U.S. Pat. No. 7,824,857 on Nov. 2, 2010 (Inventors: Mitas et al.).

Petition to Wthdraw from Issue filed Jul. 24, 2008 for U.S. Appl. No. 11/003,223, filed Dec. 2, 2004 and issued as U.S. Pat. No. 7,824,857 on Nov. 2, 2010 (Inventors: Mitas et al.).

Issue Notification issued Jul. 16, 2008 for U.S. Appl. No. 11/003,223, filed Dec. 2, 2004 and issued as U.S. Pat. No. 7,824,857 on Nov. 2, 2010 (Inventors: Mitas et al.).

Response to Rule 312 Communication issued May 5, 2008 for U.S. Appl. No. 11/003,223, filed Dec. 2, 2004 and issued as U.S. Pat. No. 7,824,857 on Nov. 2, 2010 (Inventors: Mitas et al.).

Amendment after Allowance filed Apr. 22, 2008 for U.S. Appl. No. 11/003,223, filed Dec. 2, 2004 and issued as U.S. Pat. No. 7,824,857 on Nov. 2, 2010 (Inventors: Mitas et al.).

Notice of Allowance issued Jan. 24, 2008 for U.S. Appl. No. 11/003,223, filed Dec. 2, 2004 and issued as U.S. Pat. No. 7,824,857 on Nov. 2, 2010 (Inventors: Mitas et al.).
Notice of Allowance issued Jul. 30, 2007 for U.S. Appl. No. 11/003,223, filed Dec. 2, 2004 and issued as U.S. Pat. No. 7,824,857 on Nov. 2, 2010 (Inventors: Mitas et al.).
Amendment and Response to Office Action filed May 14, 2007 for U.S. Appl. No. 11/003,223, filed Dec. 2, 2004 and issued as U.S. Pat. No. 7,824,857 on Nov. 2, 2010 (Inventors: Mitas et al.).
Non-Final Action issued Dec. 13, 2006 for U.S. Appl. No. 11/003,223, filed Dec. 2, 2004 and issued as U.S. Pat. No. 7,824,857 on Nov. 2, 2010 (Inventors: Mitas et al.).
Amendment and Response to Office Action filed Sep. 29, 2006 for U.S. Appl. No. 11/003,223, filed Dec. 2, 2004 and issued as U.S. Pat. No. 7,824,857 on Nov. 2, 2010 (Inventors: Mitas et al.).
Declaration under 37 C.F.R. § 1.132 filed Sep. 29, 2006 for U.S. Appl. No. 11/003,223, filed Dec. 2, 2004 and issued as U.S. Pat. No. 7,824,857 on Nov. 2, 2010 (Inventors: Mitas et al.).
Declaration under 37 C.F.R. § 1.132 filed Sep. 29, 2006 for U.S. Appl. No. 11/003,223, filed Dec. 2, 2004 and issued as U.S. Pat. No. 7,824,857 on Nov. 2, 2010 (Inventors: Mitas et al.).
Non-Final Rejection issued May 30, 2006 for U.S. Appl. No. 11/003,223, filed Dec. 2, 2004 and issued as U.S. Pat. No. 7,824,857 on Nov. 2, 2010 (Inventors: Mitas et al.).
Election under Restriction Requirement filed Apr. 18, 2006 for U.S. Appl. No. 11/003,223, filed Dec. 2, 2004 and issued as U.S. Pat. No. 7,824,857 on Nov. 2, 2010 (Inventors: Mitas et al.).
Restriction Requirement filed Jan. 18, 2006 for U.S. Appl. No. 11/003,223, filed Dec. 2, 2004 and issued as U.S. Pat. No. 7,824,857 on Nov. 2, 2010 (Inventors: Mitas et al.).
Notice of Abandonment issued Apr. 7, 2009 for U.S. Appl. No. 12/152,423, filed May 13, 2008 (Inventors: Mitas et al.).
Non-Final Rejection issued Sep. 26, 2008 for U.S. Appl. No. 12/152,423, filed May 13, 2008 (Inventors: Mitas et al.).
Preliminary Amendment filed May 13, 2008 for U.S. Appl. No. 12/152,423, filed May 13, 2008 (Inventors: Mitas et al.).
Notice of Abandonment issued Feb. 12, 2010 for U.S. Appl. No. 11/711,493, filed Feb. 27, 2007 (Inventors: Mitas et al.).
Non-Final Rejection issued Jul. 21, 2009 for U.S. Appl. No. 11/711,493, filed Feb. 27, 2007 (Inventors: Mitas et al.).
Response to Restriction Requirement filed May 11, 2009 for U.S. Appl. No. 11/711,493, filed Feb. 27, 2007 (Inventors: Mitas et al.).
Restriction Requirement issued Mar. 10, 2009 for U.S. Appl. No. 11/711,493, filed Feb. 27, 2007 (Inventors: Mitas et al.).
Notice of Abandonment issued Oct. 21, 2010 for U.S. Appl. No. 12/690,270, filed Jan. 20, 2010 (Inventors: Mitas et al.).
International Preliminary Report on Patentability with Written Opinion issued on Jun. 7, 2006 for PCT/US2004/040300 filed on Dec. 2, 2004 and published on Jun. 23, 2005 as WO/2005/055804 (Inventors—Mitas et al.; Applicant—MUSC Foundation for Research Development).
International Search Report issued on Jun. 29, 2005 for PCT/US2004/040300 filed on Dec. 2, 2004 and published on Jun. 23, 2005 as WO/2005/055804 (Inventors—Mitas et al.; Applicant—MUSC Foundation for Research Development).
International Preliminary Report on Patentability with Written Opinion issued on Aug. 30, 2006 for PCT/US2005/006292 filed on Feb. 25, 2005 and published on Sep. 15, 2005 as WO/2005/084254 (Inventors—Mitas et al.; Applicant—MUSC Foundation for Research Development).
International Search Report issued on Jun. 26, 2006 for PCT/US2005/006292 filed on Feb. 25, 2005 and published on Sep. 15, 2005 as WO/2005/084254 (Inventors—Mitas et al.; Applicant—MUSC Foundation for Research Development).
GenBank: AJ246858.1 for Borna disease virus mRNA for partial p10 ORF, clone 4720#1.

* cited by examiner

A. Breast #1

B. Breast #2

C. Lung

D. Colon

SEQUENCE LISTING

```
<160> NUMBER OF SEQ ID NOS: 44

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 1
ccaaatgcgg ca                                                          12

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 2
ctgcagttct gtga                                                        14

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence; note =
      synthetic construct
```

-continued

<400> SEQUENCE: 3
gcagtgactt cgt                                                        13

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 4
tgaagtacac tgg                                                        13

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 5
agccacttct gc                                                         12

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 6
tgtagctgtt gca                                                        13

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 7
gccaccatta cct                                                        13

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 8
gaaccaactc aggc                                                       14

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 9
ccaaatgcgg catcttcaaa                                              20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 10
ctgcagttct gtgagccaaa g                                            21

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 11
gcagtgactt cgtcatttgg ac                                           22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 12
tgaagtacac tggcattgac ga                                           22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 13
agccacttct gcacattgct g                                            21

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 14
tgtagctgtt gcaaatgctt taagaagaag c                                 31

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 15
gccaccatta cctgcagaaa c                                            21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence; note = synthetic construct

<400> SEQUENCE: 16
gaaccaactc aggcaggact tt                                         22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence; note = synthetic construct

<400> SEQUENCE: 17
gccgtgtgaa ccatgtgact tt                                         22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence; note = synthetic construct

<400> SEQUENCE: 18
cggatgaaac tctgagcaat gt                                         22

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence; note = synthetic construct

<400> SEQUENCE: 19
gccaacaaag ctcaggacaa c                                          21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence; note = synthetic construct

<400> SEQUENCE: 20
cgcagctcag gaagaatgtg                                            20

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence; note = synthetic construct

<400> SEQUENCE: 21
agtgctcaag gacatcgaga cg                                         22

-continued

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence; note = synthetic construct

<400> SEQUENCE: 22
gggccactgt cgcatcatga ttgg                                              24

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence; note = synthetic construct

<400> SEQUENCE: 23
accatcctat gagcgagtac cc                                                22

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence; note = synthetic construct

<400> SEQUENCE: 24
ccctggaagc ctgcaaatt                                                    19

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence; note = synthetic construct

<400> SEQUENCE: 25
accaattgca gaagac                                                       16

<210> SEQ ID NO 26
<211> LENGTH: 13
<212> TYPE: DNA
<213> ORGANISM: Artificial Sequence
<220> FEATURE:
<223> OTHER INFORMATION: Description of Artificial Sequence; note = synthetic construct

<400> SEQUENCE: 26
atccccttgg caa                                                          13

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence; note = synthetic construct

<400> SEQUENCE: 27
aaagcgcgtt gg                                                           12

<210> SEQ ID NO 28
<211> LENGTH: 12

```
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 28
gtgtgaggcc at                                                          12

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 29
aaagcgcgtt ggcgatct                                                    18

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 30
gtgtgaggcc atgcttgttt g                                                21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 31
accaattgca gaagactcag c                                                21

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 32
atccccttgg caatctgca                                                   19

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 33
ccactgctcg taaagacatt c                                                21

<210> SEQ ID NO 34
<211> LENGTH: 22
<212> TYPE: DNA
<213> ORGANISM: Artificial Sequence
```

```
<220> FEATURE:
<223> OTHER INFORMATION: Description of Artificial Sequence; note =
      synthetic construct

<400> SEQUENCE: 34
ctggtgacac agcttatgcc ct                                              22

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 35
cctggatgca gcgaatgaa                                                  19

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 36
ttgctggaac atgcgactga t                                               21

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 37
gccgtgtgaa ccatgtga                                                   18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 38
ccaaatgcgg catcttca                                                   18

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 39
catgaaagct gccttggaag a                                               21

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence; note =
``` synthetic construct

<400> SEQUENCE: 40
tgattctgcc gctcactatc ag                                              22

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 41
tgtagctgtt gcaaatgctt taagaaagaa gc                                   32

<210> SEQ ID NO 42
<211> LENGTH: 110
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 42
ccctggaagc ctgcaaattu cucugcuuga uggacuuggc ccccucccca uucaaggucu     60
ucuggacagc cucacaggga ucuugaauaa agtcctgcct gagttggttc              110

<210> SEQ ID NO 43
<211> LENGTH: 12
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 43
tgattctgcc gc                                                         12

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 44
gttcccatca atcag                                                      15

US 7,981,616 B2

ENHANCED DETECTION OF RNA USING A PANEL OF TRUNCATED GENE-SPECIFIC PRIMERS FOR REVERSE TRANSCRIPTION

CROSS REFERENCE TO RELATED APPLICATIONS

The present application claims priority to and the benefit of the filing date of U.S. Application No. 60/548,552, filed on Feb. 27, 2004, which application is incorporated herein fully by this reference.

BACKGROUND OF THE INVENTION

1. Field of the Invention

This invention relates generally to the field of diagnosing a disease by detecting gene-specific markers in a tissue sample, using RT-PCR. Specifically, the invention relates to a panel of truncated gene-specific reverse transcription primers that can enhance detection of a cancer gene in a tissue sample.

2. Background Art

Formalin-fixed, paraffin-embedded tissues (PET) are a unique source of research material with the potential of providing biological information in conjunction with known clinical outcome. Specifically, these tissues could be an ideal resource for validating newly discovered genes as diagnostic and/or prognostic molecular markers in retrospective studies. Unfortunately, RNA isolated from PET samples is considered to be a poor material for molecular analyses, since RNA is frequently degraded to 100-200 bp fragments by endogenous and exogenous ribonucleases (RNase) (1). In addition, Masuda et al have shown that RNA, and in particular the poly(A) tail of mRNA, is chemically modified, making it a poor template for cDNA synthesis (2).

Despite the technical obstacles in the analysis of PET samples, significant improvements have been made in recent years, and various studies have shown that PET samples can be used for RT-PCR analysis. The introduction of real-time RT-PCR has helped to overcome some of the difficulties of analyzing degraded RNA due to the fact that this technology has been optimized for the sensitive amplification and detection of short gene fragments (3, 1, 4). The results obtained from PET sample analysis are highly dependent on the efficiency of reverse transcription. Depending on the quality of RNA, two priming methods are commonly used in cDNA synthesis: oligo(dT) primers and random hexamers. Oligo (dT) primers anneal to the poly(A) tail of mRNA. Although this method is preferred with high quality RNA, some studies have also used it for PET analysis (5, 2). In the case of degraded mRNA, where the poly(A) tail is often fragmented and/or chemically modified (PET samples), the use of random hexamers is preferred (1, 4, 6). The major limitation of priming with random hexamers is that any RNA template, not just mRNA, can be primed.

There is a third less frequently used priming method that relies on gene-specific primers. Gene-specific reverse transcription is used to increase the specificity of the cDNA synthesis and/or enhance the detection level of low abundance RNA transcripts. Although studies have shown that gene-specific reverse transcription can increase the signal detection for a single gene (7, 8), the use of multiple gene-specific primers in a single reaction has been problematic due to the presumed formation of primer-dimers that interfere with the reverse transcription and/or subsequent PCR (9).

SUMMARY OF THE INVENTION

In accordance with the purposes of this invention, as embodied and broadly described herein, this invention, in one aspect, relates to a target-specific reverse transcription (RT) primer comprising 10-16 nucleotides.

In another aspect, the invention relates to a target-specific polymerase chain reaction (PCR) primer comprising a nucleic acid selected from the group consisting of 5'-CCAAATGCGGCA-3' (SEQ ID NO:1), 5'-CTGCAGT-TCTGTGA-3' (SEQ ID NO:2), 5'-GCAGTGACTTCGT-3' (SEQ ID NO:3), 5'-TGAAGTACACTGG-3' (SEQ ID NO:4), 5'-AGCCACTTCTGC-3' (SEQ ID NO:5), 5'-TGTAGCTGT-TGCA3' (SEQ ID NO:6), 5'-GCCACCATTACCT-3' (SEQ ID NO:7) and 5'-GAACCAACTCAGGC-3' (SEQ ID NO:8), and further comprising at least 5 additional 3' target-specific nucleotides.

In yet another aspect, the invention relates to a target-specific PCR primer, wherein the primer is selected from the group consisting of 5'-GCCGTGTGAACCATGTGACTTT ((SEQ ID NO:17), 5'-CGGATGAAACTCTGAGCAATGT (SEQ ID NO:18), 5'-GCCAACAAAGCTCAGGACAAC (SEQ ID NO:19), 5'-CGCAGCTCAGGAAGAATGTG (SEQ ID NO:20), 5'-AGTGCTCAAGGACATCGAGACG (SEQ ID NO:21), 5'-GGGCCACTGTCGCATCATGATTGG (SEQ ID NO:22), 5'-ACCATCCTATGAGCGAGTACCC (SEQ ID NO:23) and 5'-CCCTGGAAGCCTGCAAATT (SEQ ID NO:24).

In another aspect, the invention relates to a RT-PCR method comprising a) reverse transcribing RNA using a target-specific RT primer comprising 10-16 nucleotides to produce a target-specific DNA product; and b) amplifying the DNA product using a target-specific forward PCR primer and a target-specific reverse PCR primer, wherein the reverse PCR primer comprises the RT primer.

In another aspect, the invention relates to a method of detecting a cancer marker in formalin-fixed, paraffin-embedded tissue, comprising a) reverse transcribing RNA from the tissue using a marker-specific RT primer comprising 10-16 nucleotides to produce a target-specific DNA product and b) amplifying the DNA product using a marker-specific forward PCR primer and a marker-specific reverse PCR primer, wherein the reverse PCR primer comprises the RT primer, the presence of an amplification product indicating the presence of the cancer marker in the tissue.

In yet another aspect, the invention relates to a method of detecting a cancer in formalin-fixed, paraffin-embedded tissue, comprising a) reverse transcribing RNA from the tissue using an RT primer specific for a marker for the cancer, wherein the primer comprises 10-16 nucleotides, to produce a marker-specific DNA product and b) amplifying the marker-specific DNA product using a marker-specific forward PCR primer and a marker-specific reverse PCR primer, wherein the reverse PCR primer comprises the RT primer, the presence of a the marker-specific amplification product indicating the presence of the cancer in the tissue.

The present invention overcomes the problems in the art by preserving the enhanced nature of signal detection of gene-specific priming and preventing primer-dimer formation. The present invention provides novel short primers (10-16 nucleotides in length) that corresponded to the 5'-end of the reverse primer used for PCR. The use of a panel of truncated gene-specific primers during reverse transcription is superior to the use of random hexamers, ultimately resulting in significant and unexpected enhancement of gene fragment detection from PET samples containing highly degraded RNA.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE PREFERRED EMBODIMENTS

Figure 1:
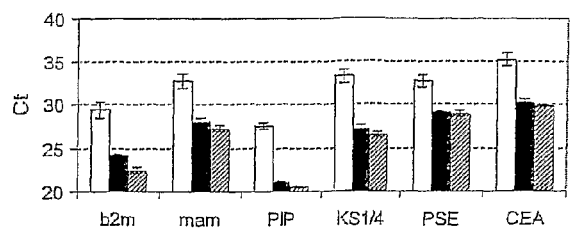
FIG. 1 shows that a panel of truncated gene-specific primers used in reverse transcription enhances gene detection in PET samples. RNA from 80 micron sections of formalin-fixed, paraffin-embedded breast (A and B), lung (C) and colon (D) cancer tissues was isolated and reverse transcribed using either random hexamers (open bars), a single gene-specific primer ($\beta_2$m, mam, pip, KS1/4, PSE, CEA; filled bars; A), or a panel of truncated gene-specific primers (striped bars). PCR was performed using primers for genes indicated in the figure. Gene detection signals are expressed as cycle threshold (Ct) values.
Figure 1:
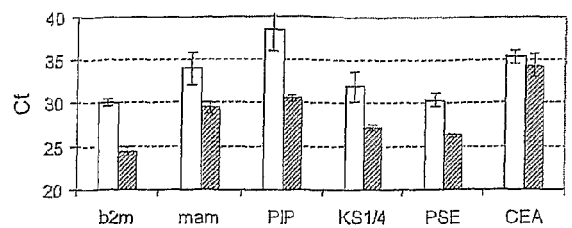
Figure 1:
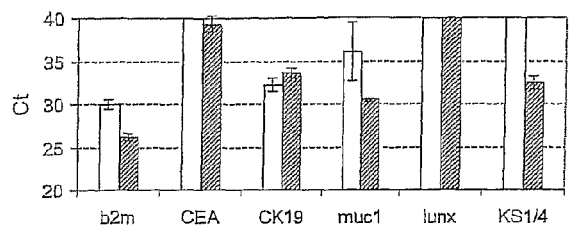
Figure 1:
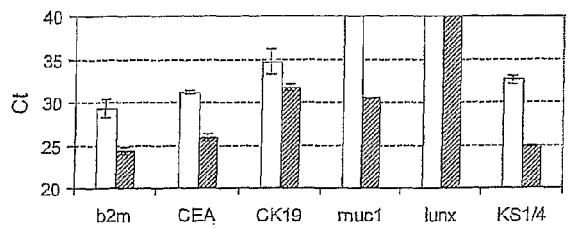

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific nucleic acids, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to a nucleic acid includes mixtures of nucleic acids.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not. For example, the phrase "optionally substituted nucleic acid" means that the nucleic acid may or may not be substituted and that the description includes both unsubstituted nucleic acid and nucleic acid where there is substitution.

The present invention provides a target-specific reverse transcription (RT) primer comprising 10-16 nucleotides. By "target-specific" or "gene-specific" is meant that the primer amplifies only a nucleic acid from a particular target nucleic acid sequence or a particular gene sequence. The RT primer of the invention can be used not only to reverse transcribe RNA in the transcription step of a reverse transcription-polymerase chain reaction (RT-PCR), but it can also be contained in a target-specific reverse PCR primer for amplification of a DNA product in a RT-PCR.

The truncated, gene-specific RT primer of this invention is the 5'-portion of a reverse PCR primer sequence, wherein the melting temperature of the RT primer is about 5° C. to about 20° C. lower than the melting temperature of the corresponding reverse PCR primer. Thus, the melting temperature of an RT primer of the invention can be 5° C., 6° C., 7° C., 8° C., 9° C., 10° C., 11° C., 12° C., 13° C., 14° C., 15° C., 16° C., 17° C., 18° C., 19° C. or 20° C. lower than the melting temperature of a corresponding PCR primer. For example, the melting temperature of an RT primer of the invention is from about 40° C. to about 42° C., and the melting temperature of a PCR primer is the typical melting temperature for a PCR primer, i.e. about 60° C. It is contemplated that the 5'-10 to 16 nucleotides of any reverse PCR primer can be identified as a functional truncated, gene-specific RT primer if the melting temperature of the 5'-10 to 16 nucleotide sequence is about 5° C. to about 20° C. lower than the melting temperature of the corresponding reverse PCR primer. Thus, for example, a person of skill can design and screen RT primers of the invention for use in the RT-PCR methods of the invention by determining that a 5'-10 to 16 nucleotides of a PCR reverse primer has a melting point from about 40° C. to about 42° C., and the melting temperature of the corresponding PCR reverse primer is about 60° C. To calculate the melting temperature of various primers, there are well-known computer programs available that take into account salt concentrations, % GC content and nucleotide length. An example of a computer program is Primer Express® software, available through ABI (Foster City, Calif.). A further routine option is to empirically calculate the melting temperature of the putative RT primer that consists of the 5' nucleotides of the reverse PCR primer to be used in the RT-PCR protocol.

As used herein, the term "nucleic acid" refers to single or multiple stranded molecules which may be DNA or RNA, or any combination thereof, including modifications to those nucleic acids. The nucleic acid may represent a coding strand or its complement, or any combination thereof. Nucleic acids may be identical in sequence to the sequences which are naturally occurring for any of the moieties discussed herein or may include alternative codons which encode the same amino acid as that which is found in the naturally occurring sequence. These nucleic acids can also be modified from their typical structure. Such modifications include, but are not limited to, methylated nucleic acids, the substitution of a non-bridging oxygen on the phosphate residue with either a sulfur (yielding phosphorothioate deoxynucleotides), selenium (yielding phosphorselenoate deoxynucleotides), or methyl groups (yielding methylphosphonate deoxynucleotides), a reduction in the AT content of AT rich regions, or replacement of non-preferred codon usage of the expression system to preferred codon usage of the expression system.

The primers of the present invention are capable of interacting with various cancer genes as disclosed herein. Representative cancer genes that can be detected by the primers of the invention include, but are not limited to, cancer genes related to breast, esophagus, lung, colon, skin, brain, bone, salivary gland, liver, stomach, pancreas, gall bladder, kidney, bladder, prostate, lymphoma, leukemia and sarcoma. The cancer genes can be detected in a primary cancerous tumor and in a secondary (metastatic) cancerous tumor.

The target-specific primers of the present invention are capable of interacting with any target nucleic acid based on the present teaching. Nucleic acids capable of detection with the present primers or methods include viral RNA or DNA (e.g., HIV, retroviruses, cytomegalovirus, adenovirus, Hepatitis A virus, Hepatitis B virus, Hepatitis C virus, Hepatitis E virus, Herpes I virus, Herpes II virus, influenza virus, polio virus, vaccinia and smallpox virus), genes upregulated in response to infection by pathogens and genes whose expression patterns are of interest. One of skill will recognize the innumerable additional targets for the present primers and methods.

In certain embodiments, the primers are used to support DNA amplification reactions. Typically the primers will be capable of being extended in a sequence-specific manner. Extension of a primer in a sequence-specific manner includes any methods wherein the sequence and/or composition of the nucleic acid molecule to which the primer is hybridized or otherwise associated directs or influences the composition or sequence of the product produced by the extension of the primer. Extension of the primer in a sequence-specific manner, therefore, includes, but is not limited to, PCR, DNA sequencing, DNA extension, DNA polymerization, RNA transcription or reverse transcription. Techniques and conditions that amplify the primer in a sequence-specific manner are preferred. In certain embodiments the primers are used for the DNA amplification reactions, such as PCR or direct sequencing. It is understood that in certain embodiments the primers can also be extended using non-enzymatic techniques where, for example, the nucleotides or oligonucleotides used to extend the primer are modified such that they will chemically react to extend the primer in a sequence specific manner. Typically, the disclosed primers hybridize with a gene or region of a gene or they hybridize with the complement of a gene or complement of a region of a gene.

The present invention provides a panel of truncated gene-specific RT primers that can be used to increase the likelihood of detecting a cancer gene in a tissue, compared to using random hexamers. To detect breast cancer, for example, a panel of primers directed to breast cancer genes $\beta_2$m, mam, PIP, KS1/4, PSE and CEA can be used. To detect lung and colon cancer, for example, a panel of primers directed to $\beta_2$m, CEA, CK19, muc1, and lunx can be used. Thus, a primer of the invention is a nucleotide sequence that is specific for a cancer gene. Such a primer that is "specific," for example, for a breast cancer gene, a lung cancer gene or a colon cancer gene is a nucleic acid that contains a sufficient number of contiguous nucleotides to be unique. To be unique, a primer of the invention must be of sufficient size to distinguish it from other known sequences, most readily determined by comparing any nucleic acid primer comprising 10-16 nucleotides to the nucleotide sequences of nucleic acids in computer databases, such as GenBank. Such comparative searches are standard in the art. The present RT primers can be at least about 10 to about 16 nucleotides in length. That is, a primer can be 10, 11, 12, 13, 14, 15 or 16 nucleotides in length. Further, the RT primers of the invention can be 12, 13 or 14 nucleotides in length. Representative examples of RT primers of the invention include, but are not limited to, CCAAATGCGGCA (SEQ ID NO:1), CTGCAGTTCTGTGA (SEQ ID NO:2), GCAGTGACTTCGT (SEQ ID NO:3), TGAAGTACACTGG (SEQ ID NO:4), AGCCACTTCTGC (SEQ ID NO:5), TGTAGCTGTTGCA (SEQ ID NO:6), GCCACCATTACCT (SEQ ID NO:7) and GAACCAACTCAGGC (SEQ ID NO:8) ACCAATTGCAGAAGAC (SEQ ID NO:25), ATCCCCTTGGCAA (SEQ ID NO:26), AAAGCGCGTTGG (SEQ ID NO:27) and GTGTGAGGCCAT (SEQ ID NO:28).

The present invention provides a reverse PCR primer comprising at its 5'-end 10 to 16 target-specific nucleotides that correspond to an RT primer to be used in conjunction with the reverse PCR primer in an RT-PCR protocol. At its 3'-end the reverse PCR primer can have about 5 to about 9 additional target-specific nucleotides. Thus, a reverse PCR primer can have 5, 6, 7, 8 or 9 additional target-specific nucleotides at its 3'-end. A nucleic acid useful as a PCR primer will be at least about 15 to about 25 nucleotides in length, depending upon the specific nucleotide content of the sequence. Thus, based on the teaching herein, a person of skill would be able to routinely design the RT and PCR primers to be used in conjunction in the present RT-PCR method. It is the relationship between the RT primer and the reverse PCR primer as described herein that provides a key advantage to the RT and PCR primers.

The present invention also provides examples of target-specific PCR primers comprising a nucleic acid selected from the group consisting of 5'-CCAAATGCGGCA-3' (SEQ ID NO:1), 5'-CTGCAGTTCTGTGA-3' (SEQ ID NO:2), 5'-GCAGTGACTTCGT-3' (SEQ ID NO:3), 5'-TGAAGTACACTGG-3' (SEQ ID NO:4), 5'-AGCCACTTCTGC-3' (SEQ ID NO:5), 5'-TGTAGCTGTTGCA3' (SEQ ID NO:6), 5'-GCCACCATTACCT-3' (SEQ ID NO:7), 5'-GAACCAACTCAGGC-3' (SEQ ID NO:8), 5'-ACCAATTGCAGAAGAC-3' (SEQ ID NO:25), 5'-ATCCCCTTGGCAA-3' (SEQ ID NO:26), 5'-AAAGCGCGTTGG-3' (SEQ ID NO:27) and 5'-GTGTGAGGCCAT-3' (SEQ ID NO:28) and further comprising at least 5 additional 3' target-specific nucleotides.

A target-specific PCR primer of the invention can be a reverse primer. Representative examples of a reverse PCR primer include, but are not limited to, 5'-CCAAATGCGGCATCTTCAAA (SEQ ID NO:9), 5'-CTGCAGTTCTGTGAGCCAAAG (SEQ ID NO:10), 5'-GCAGTGACTTCGTCATTTGGAC (SEQ ID NO:11), 5'-TGAAGTACACTGGCATTGACGA (SEQ ID NO:12), 5'-AGCCACTTCTGCACATTGCTG (SEQ ID NO:13), 5'-TGTAGCTGTTGCAAATGCTTTAAGAAGAAGC (SEQ ID NO:14), 5'-GCCACCATTACCTGCAGAAAC (SEQ ID NO:15) and 5'-GAACCAACTCAGGCAGGACTTT (SEQ ID NO:16), 5'-ACCAATTGCAGAAGACTCAGC (SEQ ID NO:31), 5'-ATCCCCTTGGCAATCTGCA (SEQ ID NO:32), 5'-AAAGCGCGTTGGCGATCT (SEQ ID NO:29) and 5'-GTGTGAGGCCATGCTTGTTTG (SEQ ID NO:30).

A target-specific forward PCR primer of the invention can be selected from the group consisting of 5'-GCCGTGT- GAACCATGTGACTTT (SEQ ID NO:17), 5'-CGGAT-GAAACTCTGAGCAATGT (SEQ ID NO:18), 5'-GCCAA-CAAAGCTCAGGACAAC (SEQ ID NO:19), 5'-CGCAGCTCAGGAAGAATGTG (SEQ ID NO:20), 5'-AGTGCTCAAGGACATCGAGACG (SEQ ID NO:21), 5'-GGGCCACTGTCGCATCATGATTGG (SEQ ID NO:22), 5'-ACCATCCTATGAGCGAGTACCC (SEQ ID NO:23) and 5'-CCCTGGAAGCCTGCAAATT (SEQ ID NO:24), 5'-CCACTGCTCGTAAAGACATTCC (SEQ ID NO:33), 5'-CTGGTGACACAGCTTATGCCCT (SEQ ID NO:34), 5'-CCTGGATGCAGCGAATGAA (SEQ ID NO:35) and 5'-TTGCTGGAACATGCGACTGAT (SEQ ID NO:36).

The present invention further provides pairs of PCR primers, comprising a forward primer and a reverse primer, that can be used in the PCR step of the RT-PCR method of the invention. Examples of the primer pairs include, but are not limited to, nucleic acids having the sequences identified as SEQ ID NO:17 and SEQ ID NO:9; SEQ ID NO:18 and SEQ ID NO:10; SEQ ID NO:19 and SEQ ID NO:11; SEQ ID NO:20 and SEQ ID NO:12; SEQ ID NO:21 and SEQ ID NO:13; SEQ ID NO:22 and SEQ ID NO:14; SEQ ID NO:23 and SEQ ID NO:15 and SEQ ID NO:24 and SEQ ID NO:16. As shown in Table 2, below, other pairs of PCR primers can be used to identify the following markers: SBEM, ErbB2, EpCam, PDEF, HoxC6 and POTE. These primer pairs can be matched with the RT primers taught herein to provide exemplary primer sets for a highly sensitive and specific RT-PCR method that can be used in a variety of tissues, but is particularly advantageous in preserved, embedded tissues.

Further provided by the present invention is an RT-PCR method comprising a) reverse transcribing RNA using a target-specific RT primer comprising 10-16 nucleotides to produce a target-specific DNA product and b) amplifying the DNA product using a target-specific forward PCR primer and a target-specific reverse PCR primer, wherein the reverse PCR primer comprises the RT primer.

The RT-PCR method can be used to detect a gene in any type of tissue whether it is preserved or non-preserved. An advantage of the present primers and RT-PCR methods is that they can be used to identify specific nucleic acids in tissue that has low levels of RNA or DNA. Tissues with low levels of nucleic acids include body fluids (e.g., peripheral blood, urine, cerebrospinal fluid, pulmonary lavage, gastric lavage, bile, vaginal secretions, seminal fluid, aqueous humor and vitreous humor). Another advantage of the present primers and RT-PCR methods is that they can be used to identify specific nucleic acids in tissues in which the nucleic acids are often highly degraded or otherwise modified from their native state. Examples of these tissues include fixed (e.g., formalin-fixed) tissues, and embedded (e.g., paraffin-embedded) tissues. Thus, the method can be used on fixed, embedded tissue, fresh tissue and fresh-frozen tissue and body fluids.

The method of the present invention can be used to amplify any specific nucleic acid target and has the same advantages over oligo(dT) primers and random hexamers in a RT-PCR, regardless of the target gene. Examples of gene targets include, but are not limited to, a breast cancer gene, for example, $\beta_2$m, mam, PIP, KS1/4, PSE, CEA, lung and colon cancer genes, for example, $\beta_2$m, CEA, CK19, muc1, and lunx and esophageal cancer, for example, $\beta_2$m, SBEM, ErbB2, EpCam, PDEF, CEA, HoxC6 and POTE. Examples of other targets include viral or other pathogens' RNA/DNA, which may be present at low levels in many tissues.

In one aspect of the RT-PCR method of the invention, the reverse PCR primer comprises the RT primer on its 5' end, and further comprises at least 5 additional target-specific nucleotides on its 3' end.

Representative examples of the reverse PCR primers comprise a nucleic acid selected from the group consisting of CCAAATGCGGCA (SEQ ID NO:1), CTGCAGTTCT-GTGA (SEQ ID NO:2), GCAGTGACTTCGT (SEQ ID NO:3), TGAAGTACACTGG (SEQ ID NO:4), AGCCACT-TCTGC (SEQ ID NO:5), TGTAGCTGTTGCA (SEQ ID NO:6), GCCACCATTACCT (SEQ ID NO:7), GAAC-CAACTCAGGC (SEQ ID NO:8), ACCAATTGCAGAA-GAC (SEQ ID NO:25), ATCCCCTTGGCAA (SEQ ID NO:26), AAAGCGCGTTGG (SEQ ID NO:27) and GTGT-GAGGCCAT (SEQ ID NO:28) on its 5' end, and further comprises at least 5 additional target-specific nucleotides on its 3' end. Thus, according to the method of the invention, a reverse PCR primer can be selected from the group of nucleic acids identified as, for example, SEQ ID NO:9, SEQ ID NO:10, SEQ ID NO:11, SEQ ID NO:12, SEQ ID NO:13, SEQ ID NO:14, SEQ ID NO:15 and SEQ ID NO:16, and the following nucleotide sequences: 5'-ACCAATTGCAGAA-GACTCAGC (SEQ ID NO:31), 5'-ATCCCCTTG-GCAATCTGCA (SEQ ID NO:32), 5'-AAAGCGCGTTG-GCGATCT (SEQ ID NO:29) and 5'-GTGTGAGGCCATGCTTGTTTG (SEQ ID NO:30).

The present invention further provides an RT-PCR method that utilizes pairs of PCR primers, comprising a forward primer and a reverse primer. Examples of the primer pairs include, but are not limited to, nucleic acids having the sequences identified as SEQ ID NO:17 and SEQ ID NO:9; SEQ ID NO:18 and SEQ ID NO:10; SEQ ID NO:19 and SEQ ID NO:11; SEQ ID NO:20 and SEQ ID NO:12; SEQ ID NO:21 and SEQ ID NO:13; SEQ ID NO:22 and SEQ ID NO:14; SEQ ID NO:23 and SEQ ID NO:15 and SEQ ID NO:24 and SEQ ID NO:16. Additional pairs of PCR primers of the invention include the following nucleotide sequences: F 5'-CCACTGCTCGTAAAGACATTCC (SEQ ID NO:33), R 5'-ACCAATTGCAGAAGACTCAGC (SEQ ID NO:31); F 5'-CTGGTGACACAGCTTATGCCCT (SEQ ID NO:34), R 5'-ATCCCCTTGGCAATCTGCA (SEQ ID NO:32); F 5'-CCTGGATGCAGCGAATGAA (SEQ ID NO:35), R 5'-AAAGCGCGTTGGCGATCT (SEQ ID NO:29); and F 5'-TTGCTGGAACATGCGACTGAT (SEQ ID NO:36), R 5'-GTGTGAGGCCATGCTTGTTTG (SEQ ID NO:30).

The RT-PCR method of the invention can utilize the PCR primer pairs, matched with the RT primers taught herein, to provide examples of a highly sensitive and specific RT-PCR method that can be used for a variety of tissues and targets, but is particularly advantageous in preserved, embedded tissues or for targets that are expected to be present at low levels.

The RT-PCR method of the invention provides a reverse transcription step that results in a mean 16 (+/−5.2)-fold increase in signal detection compared to priming with random hexamers. The reverse transcription step results in fold increases in signal detection of 1.3 for CK19, 5 for CEA, 9 for PSE, 17 to 41 for $\beta_2$m, mam, PIP and KS1/4, and 66 for muc1 compared to priming with random hexamers. That is, the mean-fold increase in signal detection compared to priming with random hexamers is from about 10.8-fold to about 21.2-fold.

Because the annealing temperatures used for the target-specific RT primers during reverse transcription are from about 40° C. to about 42° C., target-specific RT primers and target-specific PCR primers for more than one target can be used in a single reaction. The temperature range used during the RT step allows the primers to hybridize to their specific RNA template in the reverse transcription reaction, but not during the PCR step. Thus, the primers of the invention can be used as a panel of primers while preserving the enhanced nature of signal detection of gene-specific priming and preventing primer-dimer formation.

Another aspect of the invention is a method of detecting a cancer marker in a formalin-fixed, paraffin-embedded tissue, comprising a) reverse transcribing RNA from the tissue using a marker-specific RT primer comprising 10-16 nucleotides to produce a target-specific DNA product and b) amplifying the DNA product using a marker-specific forward PCR primer and a marker-specific reverse PCR primer, wherein the reverse PCR primer comprises the RT primer, the presence of an amplification product indicating the presence of the cancer marker in the tissue.

Another aspect of the invention is a method of detecting cancer in formalin-fixed, paraffin-embedded tissue, comprising a) reverse transcribing RNA from the tissue using an RT primer specific for a marker for the cancer, wherein the primer comprises 10-16 nucleotides, to produce a marker-specific DNA product and b) amplifying the marker-specific DNA product using a marker-specific forward PCR primer and a marker-specific reverse PCR primer, wherein the reverse PCR primer comprises the RT primer, the presence of a marker-specific amplification product indicating the presence of the cancer in the tissue.

A marker for a cancer, for example, breast, lung, colon and esophageal cancer, can be CK19, CEA, PSE, $\beta_2$m, mam, PIP, muc1, SBEM, ErbB2, EpCam, PDEF, HoxC6 and/or POTE.

Representative examples of forward PCR primers that can be used according to the methods of the invention include, but are not limited to, nucleic acids having the sequence identified as SEQ ID NO:17, SEQ ID NO:18, SEQ ID NO:19, SEQ ID NO:20, SEQ ID NO:21, SEQ ID NO:22, SEQ ID NO:23, SEQ ID NO:24 and the following nucleotide sequences: 5'-CCACTGCTCGTAAAGACATTCC (SEQ ID NO:33), 5'-CTGGTGACACAGCTTATGCCCT (SEQ ID NO:34), 5'-CCTGGATGCAGCGAATGAA (SEQ ID NO:35) and 5'-TTGCTGGAACATGCGACTGAT (SEQ ID NO:36).

A reverse PCR primer comprises a nucleic acid selected from the group consisting of CCAAATGCGGCA (SEQ ID NO:1), CTGCAGTTCTGTGA (SEQ ID NO:2), GCAGTGACTTCGT (SEQ ID NO:3), TGAAGTACACTGG (SEQ ID NO:4), AGCCACTTCTGC (SEQ ID NO:5), TGTAGCTGTTGCA (SEQ ID NO:6), GCCACCATTACCT (SEQ ID NO:7) and GAACCAACTCAGGC (SEQ ID NO:8), ACCAATTGCAGAAGAC (SEQ ID NO:25), ATCCCCTTGGCAA (SEQ ID NO:26), AAAGCGCGTTGG (SEQ ID NO:27) and GTGTGAGGCCAT (SEQ ID NO:28) on its 5' end, and further comprises at least about 5 to about 20 additional target-specific nucleotides on its 3' end. Thus, there can be 5, 6, 7, 8, 9, 10, 11, 12, 13, 14, 15, 16, 17, 18, 19 or 20 additional target-specific nucleotides on its 3'-end. The marker-specific RT primers and marker-specific PCR primers for more than one marker can be used in a single reaction. Representative examples of reverse PCR primers that can be used according to the methods of the invention include, but are not limited to, nucleic acids identified as SEQ ID NO:9, SEQ ID NO:10, SEQ ID NO:11, SEQ ID NO:12, SEQ ID NO:13, SEQ ID NO:14, SEQ ID NO:15, SEQ ID NO:16 and the following nucleotide sequences: 5'-ACCAATTGCAGAAGACTCAGC (SEQ ID NO:31), 5'-ATCCCCTTGGCAATCTGCA (SEQ ID NO:32), 5'-AAAGCGCGTTGGCGATCT (SEQ ID NO:29) and 5'-GTGTGAGGCCATGCTTGTTTG (SEQ ID NO:30).

Examples of PCR primer pairs of the invention that can be used to detect a cancer marker, for example, CK19, CEA, PSE, $\beta_2$m, mam, PIP, and/or muc1 include nucleic acids having the sequences identified as SEQ ID NO:17 and SEQ ID NO:9; SEQ ID NO:18 and SEQ ID NO:10; SEQ ID NO:19 and SEQ ID NO:11; SEQ ID NO:20 and SEQ ID NO:12; SEQ ID NO:21 and SEQ ID NO:13; SEQ ID NO:22 and SEQ ID NO:14; SEQ ID NO:23 and SEQ ID NO:15 and SEQ ID NO:24, SEQ ID NO:16 and the following pairs of nucleotide sequences F 5'-CCACTGCTCGTAAAGACATTCC (SEQ ID NO:33), R 5'-ACCAATTGCAGAAGACTCAGC (SEQ ID NO:31); F 5'-CTGGTGACACAGCTTATGCCCT (SEQ ID NO:34), R 5'-ATCCCCTTGGCAATCTGCA (SEQ ID NO:32); F 5'-CCTGGATGCAGCGAATGAA (SEQ ID NO:35), R 5'-AAAGCGCGTTGGCGATCT (SEQ ID NO:29); and F 5'-TTGCTGGAACATGCGACTGAT (SEQ ID NO:36), R 5'-GTGTGAGGCCATGCTTGTTTG (SEQ ID NO:30).

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

In an effort to preserve the enhanced nature of signal detection of gene-specific priming and prevent primer-dimer formation, short primers (12-14 nucleotides in length) that corresponded to the 5'-end of the reverse primer used for PCR were designed (Table 1). The annealing temperatures for the resulting primers are 40° to 42° C., a range that allows the primers to hybridize to their specific template in the reverse transcription reaction, but not during PCR.

It was hypothesized that the use of a panel of truncated gene-specific primers during reverse transcription would be superior to the use of random hexamers, ultimately resulting in significant enhancement of gene fragment detection from PET samples containing highly degraded RNA. To test this hypothesis, RNA from 20, 40, 60, and 80 micron sections of formalin-fixed, paraffin-embedded breast (n=2), colon (n=1) and lung (n=1) cancer tissues was first isolated following the method of Stanta and Schneider (7) with some modifications. PET sections were deparaffinized twice with 1 ml of xylene at 37° C. for 20 min. The pellet was washed with 0.5 mL of 100% ethanol (at 4° C.) and air-dried at room temperature. The pellet was resuspended in 140 μL of pre-chilled RNA lysis/isolation buffer and 60 μL of 20 mg/mL proteinase K, and incubated at 45° C. for one hour. RNA was extracted using an equal volume of phenol:chloroform:isoamyl (125: 24:1) solution (Sigma). The aqueous layer containing RNA was transferred to a new 1.5 mL tube. After adding 2 μg of glycogen and one volume of isopropanol, precipitation was performed at −80° C. for 1-2 hours. After centrifugation at 12,000 rpm for 30 minutes (4° C.), the RNA pellet was washed with 70% of ethanol and air-dried at room temperature. Finally, the pellet was dissolved in 50 μL of DEPC-water and stored at −20° C. RNA was quantified by spectrophotometry at 260 nm.

In reverse transcription reactions, cDNA was made from 5 μg of total RNA using either 150 ng of random hexamers or 500 ng of a panel of truncated gene-specific primers (breast cancer panel: $\beta_2$m, mam, PIP, KS1/4, PSE, CEA; lung and colon cancer panel: $\beta_2$m, CEA, CK19, muc1, lunx, KS1/4; see Table 1). RNA was reverse transcribed with 200 U of M-MLV reverse transcriptase (Promega, Madison, Wis.) in a reaction volume of 20 µL (10 min at 70° C., 50 min at 42° C., 15 min at 70° C.).

Real-time RT-PCR analyses were performed on a PE Biosystems Gene Amp® 5700 Sequence Detection System (Foster City, Calif.). The standard reaction volume was 10 µL and contained 1× QuantiTect SYBR Green PCR Master Mix (Qiagen), 0.1 U AmpErase® UNG enzyme (PE Biosystems); 0.7 µL cDNA template; and 0.25 µM of both forward and reverse primer (Table 1). The initial step of PCR was 2 min at 50° C. for AmpErase® UNG activation, followed by a 15 min hold at 95° C. Cycles (n=40) consisted of a 15 sec denaturation step at 95° C., followed by a 1 min annealing/extension step at 60° C. The final step was a 60° C. incubation for 1 min. All reactions were performed in triplicate. Real-time RT-PCR data were quantified in terms of cycle threshold (Ct) values. Ct values are inversely related to the amount of starting template; high Ct values correlate with low levels of gene expression, whereas low Ct values correlate with high levels of gene expression. The threshold for cycle of threshold (Ct) analysis was set at 0.1 relative fluorescence units. The fold difference in signal detection was calculated using the formula $AE^{\Delta Ct}$, where AE is amplification efficiency and $\Delta Ct = Ct_{random\ hexamers} - Ct_{gene\text{-}specific\ primers}$.

A representative experiment with 80 micron sections of formalin-fixed, paraffin-embedded breast, colon and lung cancer tissues is shown in FIG. 1. Overall, gene-specific priming for all samples analyzed (20, 40, 60 and 80 micron sections of four cancer tissues) resulted in an average of 16-(+/−5.2) fold increase compared to priming with random hexamers. On a per gene basis, the most significant increase was seen in muc1, where the gene expression signal increased on an average of 6 Ct units (66-fold). $\beta_2$m, mam, PIP and KS1/4 signals increased an average of 4.4 to 5.4 Ct units (17- to 41-fold). The smallest increase was seen in PSE, CEA, and CK19 signals with an average of 3.2, 2.3 and 0.6 Ct units (9-, 5- and 1.3-fold) increase, respectively. Of note, some of the gene expression signals that were undetectable (Ct=40) using random hexamers were detected using a panel of truncated gene-specific primers. For example, CEA and KS1/4 in the paraffin-embedded lung tumor (FIG. 1C), and muc1 in colon tumor (FIG. 1D) were not detected using reverse transcription with random hexamers, while priming with a panel of truncated gene-specific primers resulted in a detectable signal. Also, muc1 in lung cancer (FIG. 1.C) and PIP in one of the breast cancer specimens (FIG. 1.B) were easily detected when a panel of truncated gene-specific primers was used, whereas priming with hexamers did not always result in signal detection. The lunx gene was not detected with either random hexamers or gene-specific primers. It was also observed that using RNA from fresh frozen tissues, a panel of truncated gene-specific primers worked as well as oligo(dT) primers but better than random hexamers (an average of 4.2 (+/−1.1) Ct units increase in signal detection).

Interestingly, in cases of frozen RNA samples where results with oligo(dT) primers were poor (suggesting RNA degradation), gene-specific priming was superior to oligo (dT) and random hexamer priming. This result is consistent with the hypothesis that truncated gene-specific primers used in reverse transcription enhance the detection of gene fragments in degraded RNA samples.

To determine whether a panel of truncated gene-specific primers is as effective as a single truncated gene-specific primer, RNA from a 80 micron section of formalin-fixed, paraffin-embedded breast cancer tissue was isolated and reverse transcribed in separate reactions using: either single truncated gene-specific primers ($\beta_2$m, mam, pip, KS1/4, PSE, or CEA), or a panel of truncated gene-specific primers containing all six primers. A reaction without reverse transcriptase was included as a negative control. For each reverse transcription reaction, real-time PCR was performed using specific forward and reverse primers. In this experiment (FIG. 1A), it was observed that reverse transcription with a panel of truncated gene-specific primers was comparable in efficiency to reverse transcription with single truncated gene-specific primers, supporting the approach of simultaneous reverse transcription for multiple genes.

As demonstrated by quantitative real-time PCR, the signal detection from PET samples is significantly enhanced when a panel of truncated gene-specific primers is used, making this approach suitable for high throughput multi-marker molecular analysis. This modification facilitates the use of stored PET samples with known clinical outcome, opening an enormous resource for retrospective clinical studies to validate the use of diagnostic and/or prognostic genetic markers, and to define the genetic pathogenesis of different diseases.

TABLE 1

Primers for gene-specific reverse transcription and real-time PCR

| Gene | Sequence of selected primer pair | | Reference |
|---|---|---|---|
| β2m | F 5'-GCCGTGTGAACCATGTGACTTT | (SEQ ID NO: 17) | (10) |
| | R 5'-CCAAATGCGGCATCTTCAAA | (SEQ ID NO: 9) | |
| mam | F 5'-CGGATGAAACTCTGAGCAATGT | (SEQ ID NO: 18) | (11) |
| | R 5'-CTGCAGTTCTGTGAGCCAAAG | (SEQ ID NO: 10) | |
| PIP | F 5'-GCCAACAAAGCTCAGGACAAC | (SEQ ID NO: 19) | (11) |
| | R 5'-GCAGTGACTTCGTCATTTGGAC | (SEQ ID NO: 11) | |
| KS1/4 | F 5'-CGCAGCTCAGGAAGAATGTG | (SEQ ID NO: 20) | (12) |
| | R 5'-TGAAGTACACTGGCATTGACGA | (SEQ ID NO: 12) | |
| PSE | F 5'-AGTGCTCAAGGACATCGAGACG | (SEQ ID NO: 21) | (13) |
| | R 5'-AGCCACTTCTGCACATTGCTG | (SEQ ID NO: 13) | |
| CEA | F 5'-GGGCCACTGTCGCATCATGATTGG | (SEQ ID NO: 22) | (12) |
| | R 5'-TGTAGCTGTTGCAAATGCTTTAAGAAGAGC | (SEQ ID NO: 14) | |

TABLE 1-continued

Primers for gene-specific reverse transcription and real-time PCR

| Gene | Sequence of selected primer pair | | Reference |
|---|---|---|---|
| muc1 | F 5'-ACCATCCTATGAGCGAGTACCC | (SEQ ID NO: 23) | (11, 12) |
|  | R 5'-GCCACCATTACCTGCAGAAAC | (SEQ ID NO: 15) | |
| lunx | F 5'-CCCTGGAAGCCTGCAAATT | (SEQ ID NO: 24) | (14, 12) |
|  | R 5'-GAACCAACTCAGGCAGGACTTT | (SEQ ID NO: 16) | |

*Truncated gene-specific primers for reverse transcription (underlined sequences) correspond to 5'-end of reverse primers designed for PCR.

Example 2

According to the methods of the present invention as taught above, RT-PCR was performed to detect markers found in esophageal cancer. Table 2 provides examples of the RT and PCR primers used.

Esophageal Cancer Analysis one marker was overexpressed in 3 (43%) patients. In advanced Stage III-IV patients (n=17), at least one marker was overexpressed in 11 patients (65%). These results provide evidence that circulating tumor cells can be detected in NSCLC patients by a high throughput molecular technique. Further studies are needed to determine the clinical relevance of gene overexpression.

TABLE 2

Primers for real-time PCR and gene-specific reverse transcription

| Gene[1] | Sequences of primer pairs[2] | | Ref. | Acc. # | Size of the intron (s) |
|---|---|---|---|---|---|
| β2m | F 5'-GCCGTGTGAACCATGTGACTTT | (SEQ ID NO: 17) | (10) | NM_004048 | 626 bp |
|  | R 5'-CCAAATGCGGCATCTTCAAA | (SEQ ID NO: 9) | | | 1,246 bp |
| SBEM | F 5'-CCACTGCTCGTAAAGACATTCC | (SEQ ID NO: 33) | | AF414087 | 1,300 bp |
|  | R 5'-ACCAATTGCAGAAGACTCAGC | (SEQ ID NO: 31) | | | |
| ErbB2 | F 5'-CTGGTGACACAGCTTATGCCCT | (SEQ ID NO: 34) | | NM_004448 | 135 |
|  | R 5'-ATCCCCTTGGCAATCTGCA | (SEQ ID NO: 32) | | | |
| EpCam | F 5'-CGCAGCTCAGGAAGAATGTG | (SEQ ID NO: 20) | (12) | NM_002354 | 3,879 bp |
|  | R 5'-TGAAGTACACTGGCATTGACGA | (SEQ ID NO: 12) | | | |
| PDEF | F 5'-AGTGCTCAAGGACATCGAGACG | (SEQ ID NO: 21) | (13) | NM_012391 | 2,835 bp |
|  | R 5'-AGCCACTTCTGCACATTGCTG | (SEQ ID NO: 13) | | | |
| CEA | F 5'-GGGCCACTGTCGCATCATGATTGG | (SEQ ID NO: 22) | (12) | NM_004363 | 1,831 bp |
|  | R 5'-TGTAGCTGTTGCAAATGCTTTAAGAAGAAGC | (SEQ ID NO: 14) | | | |
| HoxC6 | F 5'-CCTGGATGCAGCGAATGAA | (SEQ ID NO: 35) | | NM_004503 | 732 bp |
|  | R 5'-AAAGCGCGTTGGCGATCT | (SEQ ID NO: 29) | | | |
| POTE | F 5'-TTGCTGGAACATGCGACTGAT | (SEQ ID NO: 36) | | NM_174981 | 1,300 bp |
|  | R 5'-GTGTGAGGCCATGCTTGTTTG | (SEQ ID NO: 30) | | | |

[1]β2m, β2-microglobin; mam, mammaglobin; PIP; prolactin-inducible protein; KS1/4, epithelial cell adhesion molecule; PSE, prostate-specific Ets factor; CEA, carcinoembryonic antigen; muc1, mucin 1; CK19, cytokeratin 19; lunx, lung and nasal epithelium carcinoma associated gene.
[2]Truncated gene-specific primers for reverse transcription (underlined sequences) correspond to 5'-end of reverse primers designed for PCR.

Example 3

Lunx is a Superior Molecular Marker for Detection of Non-Small Cell Lung Cancer in Peripheral Blood

In this example, a novel strategy was used to enrich tumor cells from the peripheral blood of 24 Stage I-IV NSCLC patients and determined expression levels for six cancer-associated genes (lunx, muc1, KS1/4, CEA, CK19, and PSE). Using thresholds established at three standard deviations above the mean observed in 15 normal controls, it was observed that lunx (10/24, 42%), muc1 (5/24, 21%), and CK19 (5/24, 21%) were overexpressed in 14/24 (58%) peripheral blood samples obtained from NSCLC patients. Patients that overexpressed either KS1/4 (n=2) or PSE (n=1) also overexpressed either lunx or muc1. In patients with presumed curable and resectable Stage I-II disease (n=7), at least Oligonucleotides. All primers were designed according to the method taught herein. In addition to having the appropriate target specificity and melting temperature, they also spanned at least one intron, and failed to amplify negative control cDNA in which reverse transcriptase enzyme was omitted. Sequences of the internal control $\beta_2$-microglobin PCR primers were: 5' GCCGTGTGAACCATGTGA (SEQ ID NO:37) (forward) and 5' CCAAATGCGGCATCTTCA (SEQ ID NO:38)(reverse). Other sequences (previously described (15) were: lunx, CCCTGGAAGCCTGCAAATT (F) (SEQ ID NO:24) GAACCAACTCAGGCAGGACTTT (R); KS1/4(SEQ ID NO:16), CGCAGCTCAGGAAGAAT-GTG (F) (SEQ ID NO:20), TGAAGTACACTGGCAT-TGACGA (R); CK19 (SEQ ID NO:12), CATGAAAGCT-GCCTTGGAAGA (F) (SEQ ID NO:39), TGATTCTGCCGCTCACTATCAG (R); CEA (SEQ ID NO:40), GGGCCACTGTCGCATCATGATTGG (F) (SEQ ID NO:22), TGTAGCTGTTGCAAATGCTTTAAGAAA-GAAGC (R); PSE (SEQ ID NO:41), AGTGCTCAAGGA-CATCGAGACG (F) (SEQ ID NO:21), AGCCACTTCTG-CACATTGCTG (R) (SEQ ID NO:13).

Synthetic lunx fragment for gene copy determination: ccctg-gaagcctgcaaattucucugcuugaug-gacuuggccccuccccauucaaggucuucuggacagccucacagggau cuugaauaaagtcctgcctgagttggttc (SEQ ID NO:42).

Peripheral Blood Specimens. Peripheral blood specimens (10-20 mL) were collected using $K_3$ EDTA tubes (Vacutainer®) and immediately placed on ice. Samples were then processed using a porous barrier density gradient centrifugation media (OncoQuick®, Hexal Gentech, Holzkirchen, Germany) per manufacturer instructions. Briefly, Pre-cooled 50 mL centrifugation tubes containing 15 mL of separation medium below a porous barrier were filled with peripheral blood and centrifuged at 1600 g for 20 min. The entire volume of the upper compartment was then collected and washed for 10 min at 200 g. Cells were pelleted and evaluated as described below.

RNA isolation and gene-specific cDNA synthesis. Total cellular RNA was isolated from pelleted cells using a guanidinium thiocyanate-phenol-chloroform solution (RNA STAT-60™; TEL-TEST, Friendswood, Tex.). Briefly, pelleted cells recovered from peripheral blood specimens were resuspended in 1 ml of RNA STAT-60™. Total RNA was isolated as per manufacturer's instructions with the exception that 1 µl of a 50 mg/ml solution of glycogen (Sigma, St. Louis, Mo.) was added to the aqueous phase prior to addition of isopropanol. Final RNA pellet was dissolved in 50 µl of 1×RNA secure buffer (Ambion, Austin, Tex.). RNA was quantified by UV absorbance at 260 nm. Complementary DNA (cDNA) was made from 5 ng of total RNA using 200 U of M-MLV reverse transcriptase (Promega, Madison, Wis.) and the following gene-specific RT primers (70 ng each): CCAAAT-GCGGCAT ($\beta_2$-microglobin) (SEQ ID NO:9), TGAAGTA-CACTGG (KS1/4) (SEQ ID NO:4), GAACCAACTCAGGC (lunx) (SEQ ID NO:8), GCCACCATTACCT (muc1) (SEQ ID NO:7), TGATTCTGCCGC (CK19) (SEQ ID NO:43), GTTCCCATCAATCAG (CEA) (SEQ ID NO:44), AGC-CACTTCTGC (PSE) (SEQ ID NO:5). Final reaction volume was 20 □l. The annealing temperature was in accordance with standard RT conditions, i.e., approximately 40-42° C.

Real-time RT-PCR. Real-time RT-PCR was performed on a PE Biosystems GeneAmp® 5700 Sequence Detection System (Foster City, Calif.). All reaction components were purchased from PE Biosystems. Standard reaction volume was 10 µl and contained 1× SYBR Green PCR Buffer, 3.5 mM $MgCl_2$, 0.2 mM each of dATP, dCTP, dGTP, and 0.4 mM of dUTP, 0.25 U AmpliTaq Gold®, 0.1 U AmpErase® UNG enzyme, 0.7 µl cDNA template, and 0.25 mM of forward and reverse primer. Initial step of RT-PCR was 2 min at 50° C. for AmpErase® UNG activation, followed by a 10-min hold at 95° C. Cycles (n=40 first round) consisted of a 15 sec melt at 95° C., followed by a 1 min annealing/extension at 60° C. The final step was a 60° C. incubation for 1 min. All reactions were performed in triplicate and a negative control lacking cDNA was included. For a blood sample to be considered evaluable, a cutoff value was set for the $\beta_2$-microglobin internal control gene at ≦25 (corresponding to approximately $2\times10^4$ gene copies).

Reliable Detection of 20 Lunx Gene Copies by Real-Time PCR.

Figure 2:
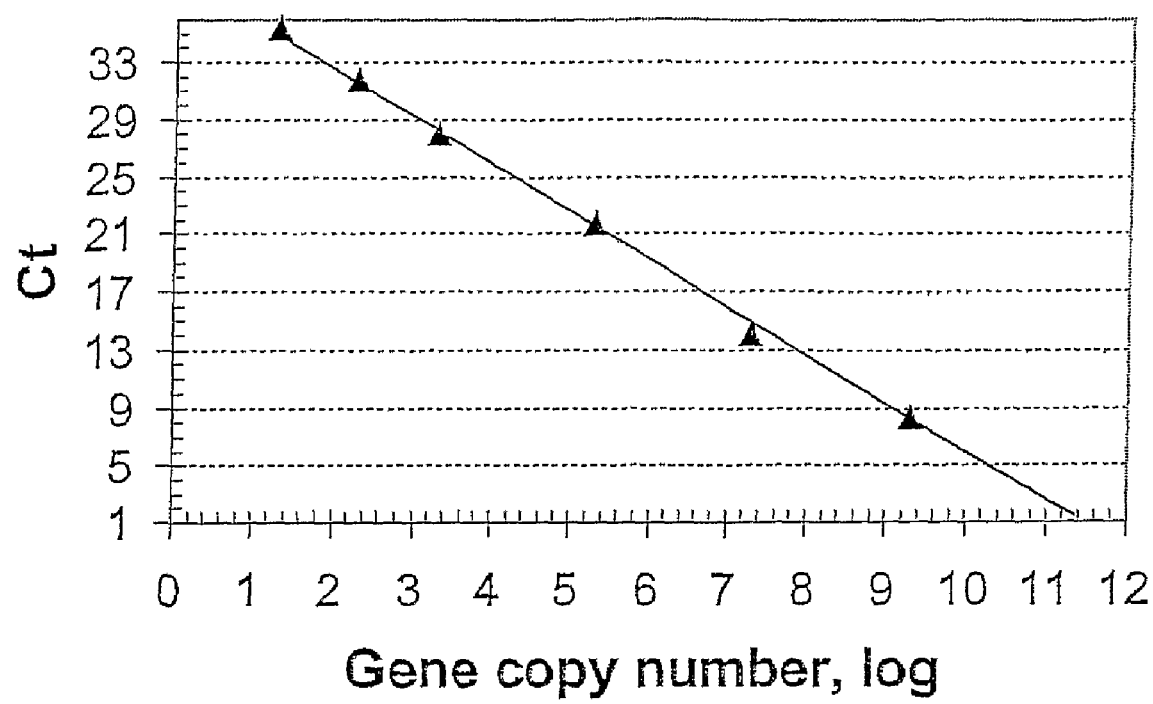
FIG. 2 shows reliable detection of 20 gene copies in a single round of PCR. Real-time RT-PCR reactions were performed in triplicate as described in Example 3 using the lunx primer pair and the lunx synthetic sequence. Gene copy number was determined by UV absorbance measurements at 260 nm. The line through the data points was obtained by linear regression analysis using Microsoft Excel® software.

To determine whether a single round of real-time RT-PCR could be used for the sensitive detection of NSCLC, studies were first performed on a synthetic fragment encoding a portion of lunx, a gene previously shown to be expressed in metastatic lymph nodes of NSCLC patients (15). $C_t$ values for various fragment dilutions were obtained and plotted as a function of initial fragment copy number. FIG. 2 demonstrates a strong linear relationship between the $C_t$ value and the log of fragment copy number ($R^2$=0.9981). Reliable fluorescent signals were obtained for reactions containing as few as 20 gene copies (FIG. 2; log value=1.4). In contrast, reliable fluorescent signals were not obtained for samples that contained only 2 gene copies, regardless of the fluorescent threshold setting used for real-time measurements. These data provide evidence that a single round (as opposed to two) of real-time PCR reliably amplifies ≧20 gene copies, a result amenable to detection of circulating tumor cells in peripheral blood.

Detection of Lunx Gene Expression in Peripheral Blood of NSCLC Patients.

To assess the ability of real-time RT-PCR to detect circulating tumor cells in the peripheral blood of NSCLC patients, samples from 15 healthy volunteers and 24 patients with Stage I-IV NSCLC were obtained. Tumor cells were first enriched from peripheral blood by a newly developed porous barrier density gradient (PBDG) centrifugation system (20). The depletion of mononuclear cells in the enriched cell fraction after PBDG centrifugation is approximately 300- to >500-fold (20, 22). Mean tumor cell recovery rates for PBDG are comparable to that achieved by ficoll purification (20, 22). Previous studies in the breast cancer setting have shown that the upper limit of detection using real-time RT-PCR is one cancer cell among $5\times10^8$ peripheral blood cells (22).

Figure 3:
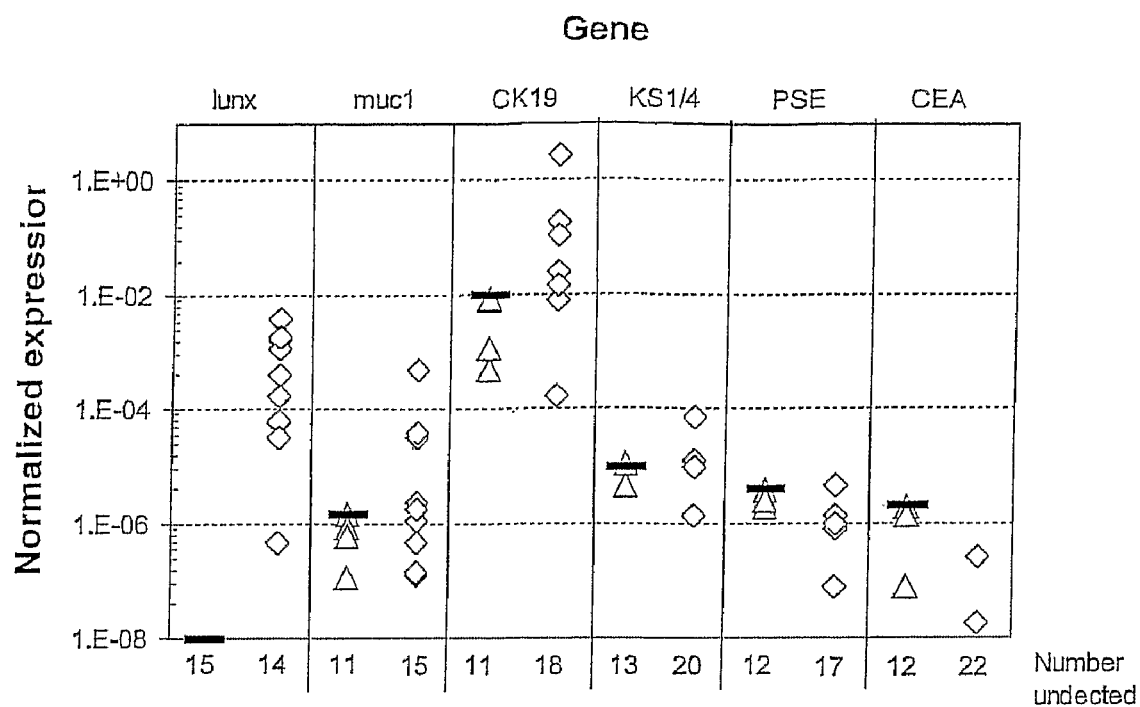
FIG. 3 shows multi-marker real-time RT-PCR analysis of NSCLC in peripheral blood. Real-time PCR analyses of peripheral blood specimens from 15 healthy volunteers (open triangles) and 24 NSCLC patients (open diamonds) were performed using primer pairs for the indicated genes. Threshold levels of marker positivity for each gene were calculated as described herein and are depicted by the horizontal line on the left side of each data set. Expression levels of each gene were calculated with Q-gene® software and are expressed as the ratio of the target gene relative to $\beta_2$-microglobin.

Using a single round of real-time PCR (40 cycles), expression levels were determined for five genes associated with NSCLC: lunx, KS1/4, muc1, CK19, and CEA (15), as well as one gene (PSE) associated with prostate (23) and breast cancer (24, 25). Mean expression levels of the cancer-associated genes were normalized to $\beta_2$-microglobin using Q-gene software (26). In the normal control peripheral blood samples, expression of the lunx gene was not detectable (FIG. 3). For other genes, expression was detected in a limited number of patients: muc1 and CK19 (four samples), CEA and PSE (3 samples), and KS1/4 (2 samples) (FIG. 3). Based on data obtained from the normal control population, threshold values were set for marker positivity at three standard deviations beyond the mean normalized expression values of each respective gene (FIG. 3; horizontal lines). Assuming a normal distribution of the control peripheral blood samples, three standard deviations correspond to a test specificity level of 99.9%. In the control patient group, no gene was overexpressed above threshold levels.

In the peripheral blood samples derived from NSCLC patients (n=24), 14/24 (58%) overexpressed at least one marker gene (FIG. 3, Table 3). The gene most highly overexpressed was lunx (10/24 samples (42%)). muc1 and CK19 were each overexpressed in 5/20 (21%) of patients, three of whom overexpressed both markers. Overexpression of KS1/4 and PSE was observed in 2 and 1 patients, respectively, all of whom overexpressed either lunx or muc1 (Table 1). In patients with presumed curable and resectable Stage I-II disease (n=7), lunx was overexpressed in 2 (29%) blood samples.

CONCLUSION

The ability to detect nucleic acid fragments by PCR is directly proportional to gene copy number, fragment amplification efficiency, and detection threshold, and inversely proportional to the formation of primer dimers. Due to their extremely low concentration (and hence, gene copy numbers), the molecular detection of cancer cells in peripheral blood has proven challenging compared to other unpreserved tissues such as lymph node. In this study, evidence was provided that the use of real-time PCR and SYBR Green I chemistry allows for reproducible detection of 20 copies of an artificial lunx sequence by PCR cycle number 36 (FIG. 2). These results provide evidence that a single round of real-time RT-PCR is sufficient for detection of genes present in low abundance.

Using a single round of real-time PCR, the peripheral blood of NSCLC patients was analyzed for expression of five genes associated with NSCLC: lunx, KS1/4, muc1, CK19, and CEA (15). With respect to normal control samples, overexpression of at least one gene was observed in 14/24 (58%) NSCLC patients. Of Stage I-III patients (n=7), 3 (43%) were positive for at least one marker, while 11/17 (65%) Stage III-V patients were marker positive. Ten NSCLC blood samples were positive for lunx, providing evidence that this marker was the most sensitive for detection of circulating NSCLC cells.

The results described in this paper provide evidence that lunx was the most sensitive marker for detection of circulating NSCLC cells.

TABLE 3

Detection of Gene Overexpression in NSCLC Patients

| Patient Information | | | Real-time RT-PCR Results[1] | | | | | |
|---|---|---|---|---|---|---|---|---|
| Pt # | Stage | Age | LUNX | MUC1 | CK19 | KS1/4 | PSE | CEA |
| 1 | IA | 78 | — | — | — | — | — | — |
| 2 | IA | 67 | 1 | — | 1 | — | — | — |
| 3 | IB | 57 | — | — | — | — | — | — |
| 4 | IB | 52 | — | — | — | — | — | — |
| 5 | IB | 75 | 1 | — | — | — | — | — |
| 6 | IIB | 75 | — | — | — | — | — | — |
| 7 | IIB | 41 | — | 1 | 1 | — | — | — |
| 8 | III | 55 | — | — | — | — | — | — |
| 9 | III | 67 | — | — | — | — | — | — |
| 10 | IIIA | 64 | — | — | — | — | — | — |
| 11 | IIIA | 71 | — | — | — | — | — | — |
| 12 | IIIB | 59 | 1 | — | — | — | — | — |
| 13 | IIIB | 63 | 1 | — | — | — | — | — |
| 14 | IIIB | 54 | 1 | 1 | 1 | — | — | — |
| 15 | IIIB | 54 | 1 | — | — | — | — | — |
| 16 | IIIB | 67 | 1 | — | — | — | — | — |
| 17 | IV | 66 | — | — | — | — | — | — |
| 18 | IV | 62 | — | 1 | — | — | — | — |
| 19 | IV | 62 | — | — | — | — | — | — |
| 20 | IV | 74 | 1 | — | — | — | — | — |
| 21 | IV | 46 | 1 | — | — | — | — | — |
| 22 | IV | 77 | — | 1 | — | — | 1 | — |
| 23 | IV | 67 | — | 1 | 1 | 1 | — | — |
| 24 | IV | 52 | 1 | — | 1 | 1 | — | — |
| Total: | | | 10 | 5 | 5 | 2 | 1 | 0 |

[1]No overexpression of the respective gene is indicated by "—"; overexpression is indicated by "1".

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

1. Specht, K., T. Richter, U. Muller, A. Walch, M. Werner and H. Hofler. 2001. Quantitative gene expression analysis in microdissected archival formalin-fixed and paraffin-embedded tumor tissue. Am J Pathol 158:419-429.
2. Masuda, N., T. Ohnishi, S. Kawamoto, M. Monden and K. Okubo. 1999. Analysis of chemical modification of RNA from formalin-fixed samples and optimization of molecular biology applications for such samples. Nucleic Acids Res 27:4436-4443.
3. Goldsworthy, S. M., P. S. Stockton, C. S. Trempus, J. F. Foley and R. R. Maronpot. 1999. Effects of fixation on RNA extraction and amplification from laser capture microdissected tissue. Mol Carcinog 25:86-91.
4. Godfrey, T. E., S. H. Kim, M. Chavira, D. W. Ruff, R. S. Warren, J. W. Gray and R. H. Jensen. 2000. Quantitative mRNA expression analysis from formalin-fixed, paraffin-embedded tissues using 5' nuclease quantitative reverse transcription-polymerase chain reaction. J Mol Diagn 2:84-91.
5. Coombs, N. J., A. C. Gough and J. N. Primrose. 1999. Optimisation of DNA and RNA extraction from archival formalin-fixed tissue. Nucleic Acids Res 27:e12.
6. Korbler, T., M. Grskovic, M. Dominis and M. Antica. 2003. A simple method for RNA isolation from formalin-fixed and paraffin-embedded lymphatic tissues. Exp Mol Pathol 74:336-340.
7. Stanta, G. and C. Schneider. 1991. RNA extracted from paraffin-embedded human tissues is amenable to analysis by PCR amplification. Biotechniques 11:304, 306, 308.
8. Corey, E. and M. J. Corey. 1998. Detection of disseminated prostate cells by reverse transcription-polymerase chain reaction (RT-PCR): technical and clinical aspects. Int J Cancer 77:655-673.
9. Dennis, P., E. A. Edwards, S. N. Liss and R. Fulthorpe. 2003. Monitoring gene expression in mixed microbial communities by using DNA microarrays. Appl Environ Microbiol 69:769-778.
10. Baker, M. K., K. Mikhitarian, W. Osta, K. Callahan, R. Hoda, F. Brescia, R. Kneuper-Hall, M. Mitas, D. J. Cole and W. E. Gillanders. 2003. Molecular detection of breast cancer cells in the peripheral blood of advanced-stage breast cancer patients using multimarker real-time reverse transcription-polymerase chain reaction and a novel porous barrier density gradient centrifugation technology. Clin Cancer Res 9:4865-4871.
11. Mitas, M., K. Mikhitarian, C. Walters, P. L. Baron, B. M. Elliott, T. E. Brothers, J. G. Robison, J. S. Metcalf, Y. Y. Palesch, Z. Zhang, W. E. Gillanders and D. J. Cole. 2001. Quantitative real-time RT-PCR detection of breast cancer micrometastasis using a multigene marker panel. Int J Cancer 93:162-171.
12. Mitas, M., D. J. Cole, L. Hoover, M. M. Fraig, K. Mikhitarian, M. I. Block, B. J. Hoffman, R. H. Hawes, W. E. Gillanders and M. B. Wallace. 2003. Real-time reverse transcription-PCR detects KS1/4 mRNA in mediastinal lymph nodes from patients with non-small cell lung cancer. Clin Chem 49:312-315.
13. Mitas, M., K. Mikhitarian, L. Hoover, M. A. Lockett, L. Kelley, A. Hill, W. E. Gillanders and D. J. Cole. 2002. Prostate-Specific Ets (PSE) factor: a novel marker for detection of metastatic breast cancer in axillary lymph nodes. Br J Cancer 86:899-904.
14. Mitas, M., L. Hoover, G. Silvestri, C. Reed, M. Green, A. T. Turrisi, C. Sherman, K. Mikhitarian, D. J. Cole, M. I. Block and W. E. Gillanders. 2003. Lunx is a superior molecular marker for detection of non-small lung cell cancer in peripheral blood. J Mol Diagn 5:237-242.
15. Mitas M, Cole D J, Hoover L, Fraig M M, Mikhitarian K, Block M I, Hoffman B J, Hawes R H, Gillanders W E, Wallace M B: Real-Time RT-PCR Detects KS1/4 mRNA in Mediastinal Lymph Nodes from Patients with Non-Small Cell Lung Cancer. Clin. Chem. 2003, 49:312-315
16. Weston W, LeClair E, Trzyna W, McHugh K, Nugent P, Lafferty C, Ma L, Tuan R, RM G: Differential display identification of plunc, a novel gene expressed in embryonic palate, nasal epithelium, and adult lung. J Biol Chem 1999, 274:13698-13703.
17. Bingle C D, Bingle L: Characterisation of the human plunc gene, a gene product with an upper airways and nasopharyngeal restricted expression pattern. Biochim Biophys Acta 2000, 1493:363-367
18. Sung Y K, Moon C, Yoo J Y, Pearse D, Pevsner J, Ronnett G V: Plunc, a member of the secretory gland protein family, is up-regulated in nasal respiratory epithelium after olfactory bulbectomy. J Biol Chem 2002, 277:12762-12769
19. Perez M S, Walker L E: Isolation and characterization of a cDNA encoding the KS1/4 epithelial carcinoma marker. J. Immunol. 1989, 142:3662-3667
20. Rosenberg R, Gertler R, Friederichs J, Fuehrer K, Dahm M, Phelps R, Thorban S, Nekarda H, Siewert J R: Comparison of Two Density Gradient Centrifugation Systems for the Enrichment of Disseminated Tumor Cells in Blood. Cytometry 2002, 49:150-158
21. Bieche I, Olivi M, Champeme M H, Vidaud D, Lidereau R, Vidaud M: Novel approach to quantitative polymerase chain reaction using real-time detection: application to the detection of gene amplification in breast cancer. Int J Cancer 1998, 78:661-666
22. Baker M, Mikhitarian K, Hoda R, Brescia F, Kneuper-Hall R, Mitas M, Cole D, Gillanders W: Molecular detection of breast cancer cells in the peripheral blood of advanced stage breast cancer patients using multi-marker real-time RT-PCR and a novel porous barrier density gradient centrifugation technology. Clin Can Res 2003, in press
23. Oettgen P, Finger E, Sun Z, Akbarali Y, Thamrongsak U, Boltax J, Grall F, Dube A, Weiss A, Brown L, Quinn G, Kas K, Endress G, Kunsch C, Libermann T A: PDEF, a novel prostate epithelium-specific ets transcription factor, interacts with the androgen receptor and activates prostate-specific antigen gene expression. J Biol Chem 2000, 275: 1216-1225
24. Ghadersohi A, Sood A K: Prostate Epithelium-derived Ets Transcription Factor mRNA Is Overexpressed in Human Breast Tumors and Is A Candidate Breast Tumor Marker and A Breast Tumor Antigen. Clin Cancer Res 2001, 7:2731-2738
25. Mitas M, Mikhitarian K, Hoover L, Lockett M A, Kelley L, Hill A, Gillanders W E, Cole D J: Prostate-specific ets (PSE) factor: a novel marker for the detection of metastatic breast cancer in axillary lymph nodes. British Journal of Cancer 2002, 86:899-905
26. Muller P Y, Janovjak H, Miserez A R, Dobbie Z: Processing of gene expression data generated by quantitative real-time RT-PCR. Biotechniques 2002, 32:1372-1374, 1376, 1378-1379

What is claimed is:

1. An RT-PCR method comprising:
   a) reverse transcribing RNA using a target-specific RT primer comprising 10-16 nucleotides to produce a target-specific DNA product; and
   b) amplifying the DNA product using a target-specific forward PCR primer and a target-specific reverse PCR primer, wherein the reverse PCR primer comprises the RT primer,
   wherein the reverse transcription step results in-fold increases in signal detection of 1.3 for CK19, 5 for CEA, 9 for PSE, 17 to 41 for $\beta_2$m, mam, PIP and KS1/4, and 66 for muc1 compared to priming with random hexamers.

2. The RT-PCR method of claim 1, wherein the method is applied to formalin fixed, paraffin-embedded tissue.

3. The RT-PCR method of claim 1, wherein the reverse PCR primer comprises the RT primer on its 5' end, and further comprises at least 5 additional target-specific nucleotides on its 3' end.

4. The RT-PCR method of claim 1, wherein the reverse transcription step utilizes an annealing temperature from about 40° C. to about 42° C.

5. The RT-PCR method of claim 1, wherein the reverse PCR primer is CCAAATGCGGCA (SEQ ID NO:1), CTG-CAGTTCTGTGA (SEQ ID NO:2), GCAGTGACTTCGT (SEQ ID NO:3), TGAAGTACACTGG (SEQ ID NO:4), AGCCACTTCTGC (SEQ ID NO:5), TGTAGCTGTTGCA (SEQ ID NO:6), GCCACCATTACCT (SEQ ID NO:7), GAACCAACTCAGGC (SEQ ID NO:8), ACCAATTGCA-GAAGAC (SEQ ID NO:25), ATCCCCTTGGCAA (SEQ ID NO:26), AAAGCGCGTTGG (SEQ ID NO:27), or GTGT-GAGGCCAT (SEQ ID NO:28) on its 5' end, and wherein the primer further comprises at least 5 additional target-specific nucleotides on its 3' end.

6. An RT-PCR method comprising:

a) reverse transcribing RNA using a target-specific RT primer comprising 10-16 nucleotides to produce a target-specific DNA product; and b) amplifying the DNA product using a target-specific forward PCR primer and a target-specific reverse PCR primer, wherein the reverse PCR primer comprises the RT primer, wherein the reverse transcription step results in a mean 16 (+/−5.2)-fold increase in signal detection compared to priming with random hexamers.

7. The method of claim 1, wherein target-specific RT primers and target-specific PCR primers for more than one target are used in a single reaction.

8. The RT-PCR method of claim 6, wherein the method is applied to formalin fixed, paraffin-embedded tissue.

9. The RT-PCR method of claim 6, wherein the reverse PCR primer comprises the RT primer on its 5' end, and further comprises at least 5 additional target-specific nucleotides on its 3' end.

10. The RT-PCR method of claim 6, wherein the reverse transcription step utilizes an annealing temperature from about 40° C. to about 42° C.

11. The RT-PCR method of claim 6, wherein the reverse PCR primer is CCAAATGCGGCA (SEQ ID NO:1), CTGCAGTTCTGTGA (SEQ ID NO:2), GCAGTGACTTCGT (SEQ ID NO:3), TGAAGTACACTGG (SEQ ID NO:4), AGCCACTTCTGC (SEQ ID NO:5), TGTAGCTGTTGCA (SEQ ID NO:6), GCCACCATTACCT (SEQ ID NO:7), GAACCAACTCAGGC (SEQ ID NO:8), ACCAATTGCAGAAGAC (SEQ ID NO:25), ATCCCCTTGGCAA (SEQ ID NO:26), AAAGCGCGTTGG (SEQ ID NO:27), or GTGTGAGGCCAT (SEQ ID NO:28) on its 5' end, and wherein the primer further comprises at least 5 additional target-specific nucleotides on its 3' end.

12. The method of claim 6, wherein target-specific RT primers and target-specific PCR primers for more than one target are used in a single reaction.

* * * * *